(12) United States Patent
Du et al.

(10) Patent No.: US 10,421,811 B2
(45) Date of Patent: Sep. 24, 2019

(54) COMPOSITIONS COMPRISING COFORMULATION OF ANTI-PD-L1 AND ANTI-CTLA-4 ANTIBODIES

(71) Applicant: MedImmune, LLC, Gaithersburg, MD (US)

(72) Inventors: Jiali Du, Gaithersburg, MD (US); Ambarish Shah, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 251 days.

(21) Appl. No.: 15/495,388

(22) Filed: Apr. 24, 2017

(65) Prior Publication Data

US 2017/0306025 A1    Oct. 26, 2017

Related U.S. Application Data

(60) Provisional application No. 62/327,214, filed on Apr. 25, 2016.

(51) Int. Cl.
| | | |
|---|---|---|
| *C07K 16/30* | (2006.01) | |
| *A61K 39/395* | (2006.01) | |
| *C07K 16/28* | (2006.01) | |
| *A61K 39/00* | (2006.01) | |

(52) U.S. Cl.
CPC ...... *C07K 16/2827* (2013.01); *A61K 39/3955* (2013.01); *A61K 39/39558* (2013.01); *A61K 39/39591* (2013.01); *C07K 16/2818* (2013.01); *C07K 16/30* (2013.01); *A61K 2039/507* (2013.01); *A61K 2039/54* (2013.01); *C07K 2317/21* (2013.01); *C07K 2317/56* (2013.01); *C07K 2317/565* (2013.01); *C07K 2317/70* (2013.01); *C07K 2317/76* (2013.01)

(58) Field of Classification Search
CPC ........ A61K 39/39591; A61K 39/39558; A61K 39/3955; C07K 16/2827; C07K 16/2818; C07K 16/30
See application file for complete search history.

(56) References Cited

U.S. PATENT DOCUMENTS 9,493,565 B2 * 11/2016 Queva ................ C07K 16/2827
2015/0328311 A1   11/2015 Narwal et al.
2016/0008485 A1   1/2016 Marquette et al.

\* cited by examiner

*Primary Examiner* — Robert C Hayes

(57) ABSTRACT

Provided herein are compositions comprising coformulation of anti-PD-L1 and anti-CTLA-4 antibodies, or antigen-binding fragments thereof, and methods of making and using such compositions. In various aspects, stable coformulations of the anti-PD-L1 antibody durvalumab (MEDI4736) and the anti-CTLA-4 antibody tremelimumab are provided.

19 Claims, 16 Drawing Sheets

Specification includes a Sequence Listing.

SEQUENCE LISTING

<160> NUMBER OF SEQ ID NOS: 16

<210> SEQ ID NO 1
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Gly Phe Thr Phe Ser Arg Tyr Trp Met Ser
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Ile Lys Gln Asp Gly Ser Glu Lys Tyr Tyr Val Asp Ser Val Lys
1               5                   10                  15

Gly

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Gly Gly Trp Phe Gly Glu Leu Ala Phe Asp Tyr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Arg Val Ser Ser Ser Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ala Ser Ser Arg Ala Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr Gly Ser Leu Pro Trp Thr
1               5

<210> SEQ ID NO 9
<211> LENGTH: 139
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
            20                  25                  30

Pro Gly Lys Ala Pro Lys Leu Leu Ile Tyr Ala Ala Ser Ser Leu Gln
        35                  40                  45

Ser Gly Val Pro Ser Arg Phe Ser Gly Ser Gly Ser Gly Thr Asp Phe
    50                  55                  60

Thr Leu Thr Ile Ser Ser Leu Gln Pro Glu Asp Phe Ala Thr Tyr Tyr
65                  70                  75                  80

Cys Gln Gln Tyr Tyr Ser Thr Pro Phe Thr Phe Gly Pro Gly Thr Lys
                85                  90                  95

Val Glu Ile Lys Arg Thr Val Ala Ala Pro Ser Val Phe Ile Phe Pro
            100                 105                 110

Pro Ser Asp Glu Gln Leu Lys Ser Gly Thr Ala Ser Val Val Cys Leu
        115                 120                 125

Leu Asn Asn Phe Tyr Pro Arg Glu Ala Lys Val
    130                 135
```

<210> SEQ ID NO 10
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
            20                  25                  30

Gly Lys Gly Leu Glu Trp Val Ala Val Ile Trp Tyr Asp Gly Ser Asn
        35                  40                  45

Lys Tyr Tyr Ala Asp Ser Val Lys Gly Arg Phe Thr Ile Ser Arg Asp
    50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Asp Pro Arg Gly Ala Thr Leu
                85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His
                165
```

```
<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Thr Phe Ser Ser Tyr Gly Met His
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Ile Trp Tyr Asp Gly Ser Asn Lys Tyr Tyr Ala Asp Ser Val
1               5                   10                  15

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Ala Val Tyr Tyr Cys Ala Arg Asp Pro Arg Gly Ala Thr Leu Tyr
1               5                   10                  15

Tyr Tyr Tyr Tyr Gly Met Asp Val
                20

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Gln Ser Ile Asn Ser Tyr Leu Asp
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ser Ser Leu Gln Ser
1               5

<210> SEQ ID NO 16
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 16

Gln Gln Tyr Tyr Ser Thr Pro Phe Thr
1               5
```

COMPOSITIONS COMPRISING COFORMULATION OF ANTI-PD-L1 AND ANTI-CTLA-4 ANTIBODIES

This application claims benefit under 35 U.S.C. § 119(e) of the following U.S. Provisional Application No. 62/327,214 filed Apr. 25, 2016. The above listed application is incorporated by reference herein in its entirety for all purposes.

SEQUENCE LISTINGS

The instant application contains a Sequence Listing which has been submitted electronically in ASCII format and is hereby incorporated by reference in its entirety. Said ASCII copy, created on Apr. 24, 2017, is named TRB7-300-US-NP_SL.txt and is 8,462 bytes in size.

BACKGROUND

Cancer continues to be a major global health burden. Despite progress in the treatment of cancer, there continues to be an unmet medical need for more effective and less toxic therapies, especially for those patients with advanced disease or cancers that are resistant to existing therapeutics.

The role of the immune system, in particular T cell-mediated cytotoxicity, in tumor control is well recognized. There is mounting evidence that T cells control tumor growth and survival in cancer patients, both in early and late stages of the disease. However, tumor-specific T-cell responses are difficult to mount and sustain in cancer patients.

Two T cell pathways receiving significant attention to date signal through Cytotoxic T-lymphocyte-associated antigen-4 (CTLA-4, CD152) and Programmed cell death ligand-1 (PD-L1, also known as B7-H1 or CD274).

CTLA-4 is expressed on activated T cells and serves as a co-inhibitor to keep T cell responses in check following CD28-mediated T cell activation. CTLA-4 is believed to regulate the amplitude of the early activation of naïve and memory T cells following TCR engagement and to be part of a central inhibitory pathway that affects both antitumor immunity and autoimmunity. CTLA-4 is expressed exclusively on T cells, and the expression of its ligands CD80 (B7.1) and CD86 (B7.2), is largely restricted to antigen-presenting cells, T cells, and other immune mediating cells. Antagonistic anti-CTLA-4 antibodies that block the CTLA-4 signaling pathway have been reported to enhance T cell activation. One such antibody, ipilimumab, was approved by the FDA in 2011 for the treatment of metastatic melanoma. Another anti-CTLA-4 antibody, tremelimumab, was tested in phase III trials for the treatment of advanced melanoma, but did not significantly increase the overall survival of patients compared to the standard of care (temozolomide or dacarbazine) at that time.

PD-L1 is also part of a complex system of receptors and ligands that are involved in controlling T-cell activation. In normal tissue, PD-L1 is expressed on T cells, B cells, dendritic cells, macrophages, mesenchymal stem cells, bone marrow-derived mast cells, as well as various nonhematopoietic cells. Its normal function is to regulate the balance between T-cell activation and tolerance through interaction with its two receptors: Programmed cell death-1 (also known as PD-1 or CD279) and CD80 (also known as B7.1 or B7-1). PD-L1 is also expressed by tumors and acts at multiple sites to help tumors evade detection and elimination by the host immune system. PD-L1 is expressed in a broad range of cancers with a high frequency. In some cancers, expression of PD-L1 has been associated with reduced survival and unfavorable prognosis. Antibodies that block the interaction between PD-L1 and its receptors are able to relieve PD-L1-dependent immunosuppressive effects and enhance the cytotoxic activity of antitumor T cells in vitro. Durvalumab (MEDI4736) is a human monoclonal antibody directed against human PD-L1 that is capable of blocking the binding of PD-L1 to both the PD-1 and CD80 receptors.

Improving survival of cancer patients remains difficult despite advances in medical treatment. Combination immunotherapies have the potential to be effective. However, current methods of combination therapy involve separate administration of individual drugs. It would be useful and desirable to be able to administer multiple therapeutic proteins in a single formulation, for example to facilitate delivery. However, drug stability, drug purity, drug compatibility, effective dose concentrations (e.g., to achieve pharmacodynamic and/or pharmacokinetic parameters; to avoid adverse effects or drug toxicity), and/or compatible pharmaceutically acceptable excipients represent important considerations for multi-drug formulations. Accordingly, there is an urgent need for multi-drug product formulations and methods of making them.

SUMMARY OF THE INVENTION

The invention provides a robust coformulation design space within which two monoclonal antibodies (mAbs) are formulated at different protein concentration ratios. Anti-PD-L1 antibody (e.g., durvalumab) and anti-CTLA-4 antibody (e.g., tremelimumab) were formulated into individually stable formulations and mixed to achieve a design space of new liquid and lyophilized coformulations at various anti-PD-L1 to anti-CTLA-4 concentration ratios.

In one aspect, the invention provides a composition containing an anti-PD-L1 antibody (e.g., durvalumab), or an antigen-binding fragment thereof, and an anti-CTLA-4 antibody (e.g., tremelimumab), or an antigen-binding fragment thereof, where the concentration of the anti-PD-L1, or antigen-binding fragment thereof, is about 18.7 mg/mL to about 44.4 mg/mL and the concentration of the anti-CTLA-4 antibody, or antigen-binding fragment thereof, is about 2.2 mg/mL to about 12.5 mg/mL.

In another aspect, the invention provides a composition containing durvalumab, or an antigen-binding fragment thereof, and tremelimumab, or an antigen-binding fragment thereof, where the concentration of durvalumab, or an antigen-binding fragment thereof, is about 18.7 mg/mL to about 44.4 mg/mL and where the concentration of tremelimumab, or an antigen-binding fragment thereof, is about 2.2 mg/mL to about 12.5 mg/mL.

In another aspect, the invention provides a composition containing or consisting of about 18.7 mg/mL durvalumab, or antibody fragment thereof, about 12.5 mg/mL tremelimumab, or antibody fragment thereof, about 22 mM Histidine/Histidine-HCl, about 254 mM Trehalose dehydrate, about 0.17 mM EDTA, and about 0.02% w/v PS80 at a pH of about 5.8.

In another aspect, the invention provides a composition containing or consisting of about 28.6 mg/mL durvalumab, or antibody fragment thereof, about 8.6 mg/mL tremelimumab, or antibody fragment thereof, about 23 mM Histidine/Histidine-HCl, about 252 mM Trehalose dehydrate, about 0.12 mM EDTA, and about 0.02% w/v PS80 at a pH of about 5.8.

In another aspect, the invention provides a composition containing or consisting of about 36.3 mg/mL durvalumab, or antibody fragment thereof, about 5.5 mg/mL tremelimumab, or antibody fragment thereof, about 24 mM Histidine/Histidine-HCl, about 260 mM Trehalose dehydrate, about 0.07 mM EDTA, and about 0.02% w/v PS80 at a pH of about 6.0

In another aspect, the invention provides a composition containing or consisting of about 40.0 mg/mL durvalumab, or antibody fragment thereof, about 4.0 mg/mL tremelimumab, or antibody fragment thereof, about 25 mM Histidine/Histidine-HCl, about 264 mM Trehalose dehydrate, about 0.05 mM EDTA, and about 0.02% w/v PS80 at a pH of about 6.0.

In another aspect, the invention provides a composition containing or consisting of about 42.8 mg/mL durvalumab, or antibody fragment thereof, about 2.9 mg/mL tremelimumab, or antibody fragment thereof, about 25 mM Histidine/Histidine-HCl, about 267 mM Trehalose dehydrate, about 0.04 mM EDTA, and about 0.02% w/v PS80 at a pH of about 6.0.

In another aspect, the invention provides a composition containing or consisting of about 44.4 mg/mL durvalumab, or antibody fragment thereof, about 2.2 mg/mL tremelimumab, or antibody fragment thereof, about 25 mM Histidine/Histidine-HCl, about 269 mM Trehalose dehydrate, about 0.03 mM EDTA, and about 0.02% w/v PS80 at a pH of about 6.0.

In another aspect, the invention provides a composition containing or consisting of about 44.4 mg/mL durvalumab, or antibody fragment thereof, about 2.2 mg/mL tremelimumab, or antibody fragment thereof, about 25 mM Histidine/Histidine-HCl, about 269 mM Trehalose dehydrate, about 0.03 mM EDTA, and about 0.02% w/v PS80 at a pH of about 6.0.

In another aspect, the invention provides a method of making the composition according to any aspect delineated herein, the method involving mixing an anti-PD-L1 antibody (e.g., durvalumab), or antigen-binding fragment thereof, and an anti-CTLA-4 antibody (e.g., tremelimumab), or antigen-binding fragment thereof, to obtain a concentration of anti-PD-L1 antibody, or antigen-binding fragment thereof, of about 18.7 mg/mL to about 44.4 mg/mL, and a concentration of anti-CTLA-4 antibody, or antigen-binding fragment thereof, of about 2.2 mg/mL to about 12.5 mg/mL.

In another aspect, the invention provides a method of treatment involving administering to a subject (e.g., a patient) the composition according to any aspect delineated herein.

In another aspect, the invention provides a kit including the composition according to any aspect delineated herein, and instructions for use in the method of any aspect delineated herein (e.g., in the treatment of a solid tumor, cancer, lung cancer, or non-small cell lung cancer (NSCLC)).

In various embodiments of any aspect delineated herein, the concentration of the anti-PD-L1 antibody, or antigen-binding fragment thereof, is about 18.7 mg/mL, 28.6 mg/mL, 36.3 mg/mL, 40.0 mg/mL, 42.8 mg/mL, or 44.4 mg/mL. In various embodiments of any aspect delineated herein, the concentration of the anti-CTLA-4 antibody, or antigen-binding fragment thereof, is about 2.2 mg/mL, 2.9 mg/mL, 4.0 mg/mL, 5.5 mg/mL, 8.6 mg/mL, or 12.5 mg/mL.

In various embodiments of any aspect delineated herein, the combined concentration of the anti-PD-L1, or antigen-binding fragment thereof, and the anti-CTLA-4 antibody, or antigen-binding fragment thereof, is about 31.2 mg/mL to about 46.6 mg/mL. In certain embodiments, the combined concentration of the anti-PD-L1, or antigen-binding fragment thereof, and the anti-CTLA-4 antibody, or antigen-binding fragment thereof, is about 31.2 mg/mL, 37.1 mg/mL, 41.8 mg/mL, 44.0 mg/mL, 45.7 mg/mL, or 46.6 mg/mL.

In various embodiments of any aspect delineated herein, the concentration ratio of the anti-PD-L1 antibody, or antigen-binding fragment thereof, to the anti-CTLA-4 antibody, or antigen-binding fragment thereof, is about 15:10 to about 20:1. In certain embodiments, the concentration ratio of the anti-PD-L1 antibody, or antigen-binding fragment thereof, to the anti-CTLA-4 antibody, or antigen-binding fragment thereof, is about 15:10, 10:3, 20:3, 10:1, 15:1, or 20:1.

In various embodiments of any aspect delineated herein, the anti-PD-L1 antibody is durvalumab. In various embodiments of any aspect delineated herein, the anti-CTLA-4 antibody is tremelimumab. In various embodiments of any aspect delineated herein, the anti-PD-L1 antibody is durvalumab and the anti-CTLA-4 antibody is tremelimumab.

In various embodiments of any aspect delineated herein, the concentration of durvalumab, or an antigen-binding fragment thereof, is about 18.7 mg/mL, 28.6 mg/mL, 36.3 mg/mL, 40.0 mg/mL, 42.8 mg/mL, or 44.4 mg/mL. In various embodiments of any aspect delineated herein, the concentration of tremelimumab, or an antigen-binding fragment thereof, is about 2.2 mg/mL, 2.9 mg/mL, 4.0 mg/mL, 5.5 mg/mL, 8.6 mg/mL, or 12.5 mg/mL.

In various embodiments of any aspect delineated herein, the combined concentration of durvalumab, or an antigen-binding fragment thereof, and tremelimumab, or an antigen-binding fragment thereof, is about 31.2 mg/mL to about 46.6 mg/mL. In certain embodiments, the combined concentration of durvalumab, or an antigen-binding fragment thereof, and tremelimumab, or an antigen-binding fragment thereof, is about 31.2 mg/mL, 37.1 mg/mL, 41.8 mg/mL, 44.0 mg/mL, 45.7 mg/mL, or 46.6 mg/mL.

In various embodiments of any aspect delineated herein, the concentration ratio of durvalumab to tremelimumab is from about 15:10 to about 20:1. In certain embodiments, the concentration ratio is about 15:10, 10:3, 20:3, 10:1, 15:1, or 20:1.

In various embodiments of any aspect delineated herein, the composition contains Histidine, Histidine-HCl, or a combination thereof. In various embodiments, the concentration of Histidine, Histidine-HCl, or a combination thereof, is from about 20 mM to about 25 mM.

In various embodiments of any aspect delineated herein, the composition contains trehalose dihydrate. In certain embodiments, the concentration of trehalose dihydrate is from about 254 mM to about 269 mM.

In various embodiments of any aspect delineated herein, the composition contains disodium edetate dihydrate (EDTA disodium salt dihydrate). In certain embodiments, the concentration of EDTA is from about 0.03 mM to about 0.27 mM.

In various embodiments of any aspect delineated herein, the composition contains polysorbate 80 (PS80). In certain embodiments, the concentration of polysorbate 80 is about 0.02 percent weight/volume (% w/v).

In various embodiments of any aspect delineated herein, the composition has a pH of about 6.0.

In various embodiments of any aspect delineated herein, the composition is formulated for intravenous injection. In various embodiments of any aspect delineated herein, the subject has one or more of a solid tumor, cancer, lung cancer, or non-small cell lung cancer (NSCLC). In various embodiments of any aspect delineated herein, the composition is administered by intravenous injection.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

It is to be noted that the term "a" or "an" entity refers to one or more of that entity; for example, "an antibody" is understood to represent one or more antibodies. As such, the terms "a" (or "an"), "one or more," and "at least one" can be used interchangeably herein.

The term "antibody," as used in this disclosure, refers to an immunoglobulin or a fragment or a derivative thereof, and encompasses any polypeptide comprising an antigen-binding site, regardless whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')$_2$, Fv, scFv, Fd, dAb, and other antibody fragments that retain antigen-binding function. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant." An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')2 fragment in which the two arms of the antibody molecule remain linked and comprise two-antigen binding sites. The F(ab')2 fragment has the ability to cros slink antigen. "Fv" when used herein refers to the minimum fragment of an antibody that retains both antigen-recognition and antigen-binding sites. "Fab" when used herein refers to a fragment of an antibody that comprises the constant domain of the light chain and the CHI domain of the heavy chain.

The term "mAb" refers to monoclonal antibody. Antibodies of the invention comprise without limitation whole native antibodies, bispecific antibodies; chimeric antibodies; Fab, Fab', single chain V region fragments (scFv), fusion polypeptides, and unconventional antibodies.

In this disclosure, "comprises," "comprising," "containing" and "having" and the like can have the meaning ascribed to them in U.S. Patent law and can mean " includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected. In one embodiment, the analyte is a protein and the detection method measures a physicochemical property of the protein.

By "effective amount" refers to a dosage or amount of an agent that is sufficient to result in amelioration of symptoms in a patient or to achieve a desired biological outcome. In one embodiment, an effective amount is used to treat non-small cell lung cancer (NSCLC).

By "reference" is meant a standard of comparison. In one embodiment, a reference as used herein refers to a physicochemical property of a protein that is not coformulated with another protein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION

Figure 1:
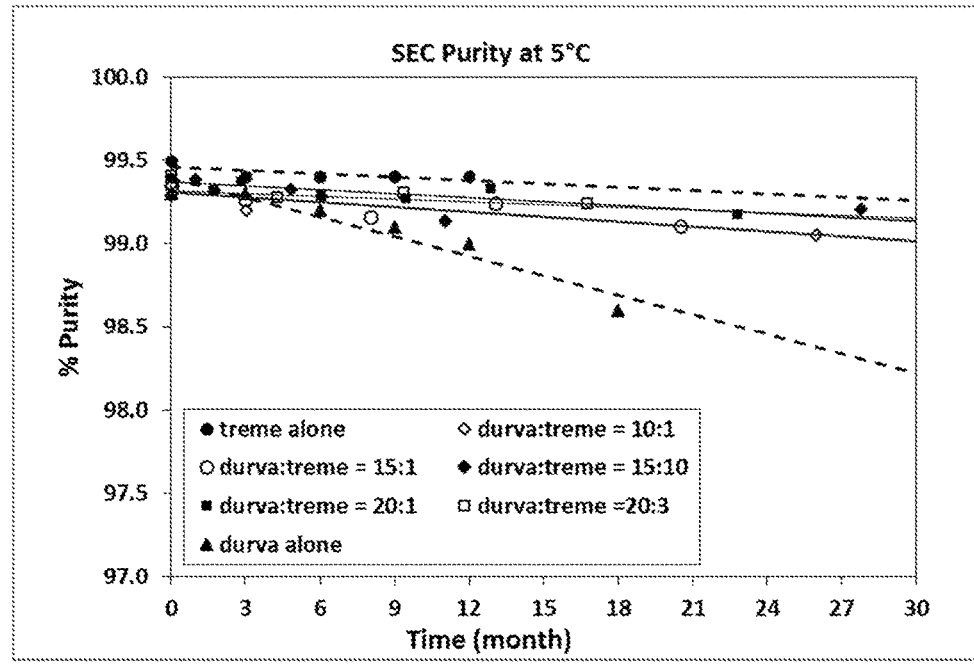
FIG. 1 is a graph depicting purity of coformulated durvalumab/tremelimumab as assessed by high performance size exclusion chromatography (HPSEC) at various concentration ratios when compared to durvalumab alone or tremelimumab alone at 5° C.

The invention features compositions comprising a coformulation of at least two antibodies (e.g., anti-PD-L1 and anti-CTLA-4 antibodies) and methods of making and using such coformulations. In particular, the coformulations are useful for parenteral (e.g. intravenous) drug administration.

The present invention is based, at least in part, on the discovery of a robust coformulation design space within which two monoclonal antibodies (e.g., anti-PD-L1 and anti-CTLA-4 antibodies) are formulated at different protein concentration ratios. As reported in detail below, a study was conducted to find compatible and stable coformulations having different protein concentrations of the anti-PD-L1 antibody durvalumab and anti-CTLA-4 antibody tremelimumab.

Anti-PD-L1 and anti-CTLA-4 antibodies were formulated into individually stable formulations. Upon mixing, the final coformulation varied based on the target final protein concentration ratios between the two antibodies. The stability profiles of coformulated antibodies at different protein concentration ratios were compared to that of the corresponding individual antibodies. Surprisingly and advantageously, the antibodies of the coformulations were found to be stable, without perturbing quality attributes of the antibodies, and compatible with the excipients of the coformulations. Thus, a design space of new liquid coformulations was derived with the anti-PD-L1 antibody durvalumab and anti-CTLA-4 antibody tremelimumab at different protein concentration ratios. Stable coformulations established in this invention include anti-PD-L1 (durvalumab) to anti-CTLA-4 (tremelimumab) concentration ratios of 10:1, 15:1, 15:10, 20:1, as well as 20:3. Thus, it was demonstrated the coformulation of these two antibodies was robust and the stability of the two antibodies was maintained over the tested range of protein concentration ratios.

Antibody Coformulation Compositions

The invention features coformulation compositions comprising anti-PD-L1 and anti-CTLA-4 antibodies, or antibody fragments thereof. In certain embodiments, the anti-PD-L1 antibody durvalumab and anti-CTLA-4 antibody tremelimumab are coformulated. Durvalumab (MEDI4736) is a selective, high-affinity human IgG1 monoclonal antibody (mAb) that blocks PD-L1 binding to PD-1 and CD80. In an ongoing Phase ½ study, durvalumab monotherapy has produced durable responses in patients with advanced NSCLC, with a manageable tolerability profile. Disclosure related to durvalumab can be found in U.S. Pat. Nos. 8,779,108 and 9,493,565. Tremelimumab (CP-675,206) is a selective human IgG2 mAb inhibitor of CTLA-4 that promotes T cell activity through CTLA-4 inhibition, but does not appear to directly deplete regulatory T cells. Disclosure related to tremelimuab can be found in U.S. Pat. No 6,682,736. The combination of durvalumab and tremelimumab is based on strong preclinical data indicating that the two pathways are non-redundant, which suggests that targeting both may have additive or synergistic effects. For the formulations detailed herein, it should be noted that the antibody or antibody fragment in the composition or formulation retains the desired biological activity and/or retains the desired physicochemical characteristics. In various embodiments, the formulations of the disclosure comprise water or one or more suitable solvents. In various embodiments, the water is distilled. In certain embodiments, the formulations include one or more additional components, such as excipients. In preferred embodiments, the antibody formulations of the disclosure are sterile and/or pyrogen-free, such as is suitable for injection into a subject. Methods for the preparation of pharmaceutical compositions are known in the art and described, for example, by Remington's Pharmaceutical Sciences (Mack Publishing Co.) 16th ed. (1980), which is incorporated herein by reference.

The concentration and/or proportions of each of these components of the formulation is detailed herein. It should be understood that the disclosure contemplates formulations comprising any combination of the specific concentrations of components set forth herein. Additionally, for formulations that may optionally comprise other excipients, it should be understood that the description contemplates formulations comprising any combination of these features.

In various embodiments, the composition or coformulation contains anti-PD-L1 antibody (e.g., durvalumab), or antibody fragment thereof, at a concentration of about 18.7 mg/mL to about 44.4 mg/mL and anti-CTLA-4 antibody (tremelimumab), or antibody fragment thereof, at a concentration of about 2.2 mg/mL to about 12.5 mg/mL. In other embodiments, the composition or coformulation contains anti-PD-L1 antibody (e.g., durvalumab), or antibody fragment thereof, at a concentration of about 18.0 mg/mL to about 45 mg/mL and anti-CTLA-4 antibody (tremelimumab), or antibody fragment thereof, at a concentration of about 2.0 mg/mL to about 15.0 mg/mL. In certain embodiments, the composition or coformulation contains anti-PD-L1 antibody (e.g., durvalumab), or antibody fragment thereof, at a concentration of about 18.7 mg/mL, 36.3 mg/mL, 40.0 mg/mL, 42.8 mg/mL, or 44.4 mg/mL. In other embodiments, the concentration of anti-PD-L1 antibody (e.g., durvalumab), or antibody fragment thereof, is about 18.0, 27.0, 36.0, or 45.0 mg/mL. In other embodiments, the concentration of anti-PD-L1 antibody (e.g., durvalumab), or antibody fragment thereof, is about 20.0, 25.0, 30.0, 35.0, 40.0, or 45.0 mg/mL. In certain embodiments, the composition or coformulation contains anti-CTLA-4 antibody (e.g., tremelimumab), or antibody fragment thereof, at a concentration of about 2.2 mg/mL, 2.9 mg/mL, 4.0 mg/mL, 5.5 mg/mL, or 12.5 mg/mL. In other embodiments, the concentration of anti-CTLA-4 antibody (e.g., tremelimumab), or antibody fragment thereof, is about 2.0, 3.0, 4.0, 5.0, 6.0, 7.0, 8.0, 9.0, 10.0, 11.0, 12.0, 13.0, 14.0, or 15.0 mg/mL.

In specific embodiments, the composition or coformulation contains about 18.7 mg/mL anti-PD-L1 antibody (e.g., durvalumab), or antibody fragment thereof, and about 12.5 mg/mL anti-CTLA-4 antibody (tremelimumab), or antibody fragment thereof; about 36.3 mg/mL anti-PD-L1 antibody (e.g., durvalumab), or antibody fragment thereof, and about 5.5 mg/mL anti-CTLA-4 antibody (tremelimumab), or antibody fragment thereof; about 40.0 mg/mL anti-PD-L1 antibody (e.g., durvalumab), or antibody fragment thereof, and about 4.0 mg/mL anti-CTLA-4 antibody (tremelimumab), or antibody fragment thereof; about 42.8 mg/mL anti-PD-L1 antibody (e.g., durvalumab), or antibody fragment thereof, and about 2.9 mg/mL anti-CTLA-4 antibody (tremelimumab), or antibody fragment thereof; or about 44.4 mg/mL anti-PD-L1 antibody (e.g., durvalumab), or antibody fragment thereof, and about 2.2 mg/mL anti-CTLA-4 antibody (tremelimumab), or antibody fragment thereof.

In various embodiments, the protein concentration ratio of the anti-PD-L1 antibody (durvalumab), or antibody fragment thereof, to the anti-CTLA-4 antibody (e.g., tremelimumab), or antibody fragment thereof, is about 15:10 to about 20:1. In particular embodiments, the protein concentration ratio of the anti-PD-L1 antibody, or antibody fragment thereof, to the anti-CTLA-4 antibody, or antibody fragment thereof, is about 15:10, 20:3, 10:1, 15:1, or 20:1. It is appreciated by the ordinarily skilled person that the protein concentration ratio can be used to obtain a protein concentration for a fragment of an antibody corresponding to a protein concentration of the antibody, for example, taking into account the difference in molecular weight between the antibody and the antibody fragment thereof.

In some embodiments, the composition or formulation may contain histidine with a concentration ranging from about 1 mM to about 50 mM, or about 20 mM to about 30 mM, or about 22 mM to about 25 mM. In specific embodiments, the concentration of histidine is about 20, 21, 22, 23, 24, 25, 26, 27, 28, 29, or 30 mM. Histidine can be in the form of L-histidine, D-histidine, or a mixture thereof. Histidine can be also in the form of hydrates. Histidine may be used in a form of pharmaceutically acceptable salt, such as hydrochloride (e.g., monohydrochloride and dihydrochloride), hydrobromide, sulfate, acetate, etc. The purity of histidine should be at least 98%, or at least 99%, or at least 99.5%. Histidine acts as a buffer in solutions having a pH of about 5.5 to about 6.0.

The compositions or formulations may further comprise excipients, such as saccharides (e.g., sucrose, mannose, trehalose, etc.), polyols (e.g., Tween) and/or sugar alcohols (e.g., mannitol, sorbitol, etc.). In one embodiment, the excipient is a saccharide. In a specific embodiment, the saccharide is trehalose (e.g., trehalose dehydrate), which is at a concentration ranging from between about 200 mM to about 300 mM, or about 225 mM to about 275 mM, about 250 mM to about 270 mM, or about 254 to about 269 mM. In specific embodiments, the concentration of saccharide (e.g., trehalose dehydrate) is about 250, 251, 252, 253, 254, 255, 256, 257, 258, 259, 260, 261, 262, 263, 264, 265, 266, 267, 268, 269, or 270 mM. In another embodiment, the excipient is a polyol. In specific embodiments, the polyol is polysorbate (e.g., polysorbate 80), which is at a concentration ranging from between about 0.01% (w/v) to about 1.0% (w/v) or about 0.02% (w/v) to about 0.05% (w/v). In specific embodiments, the concentration of polysorbate (e.g., polysorbate 80) is at a concentration of about 0.01%, 0.02%, 0.03%, 0.04%, 0.05%, 0.06%, 0.07%, 0.08%, 0.09%, or 1.0% (w/v).

The compositions or formulations may further comprise a preservative (e.g., an antimicrobial preservative). In various embodiments, the compositions or formulations comprise disodium edetate dihydrate (EDTA disodium salt dihydrate). In certain embodiments, the concentration of EDTA is from about 0.01 mM to about 0.3 mM, about 0.03 to about 0.17, or about 0.03 mM to about 0.3 mM. In specific embodiments, the concentration of EDTA is about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, or 0.30 mM.

The pH of the formulation generally should not be equal to the isoelectric point of the particular antibodies (including antibody fragments thereof) and may range from about 4.0 to about 7.0, about 5.0 to about 6.0, or about 5.5 to about 6.0. In certain embodiments, the composition or formulation of the present disclosure has a pH of about 5.5, 5.6, 5.7, 5.8, 5.9, or 6.0.

In various embodiments, the composition or formulation of the present disclosure comprises an anti-PD-L1 antibody (e.g., durvalumab), or antibody fragment thereof, an anti-CTLA-4 antibody (tremelimumab), or antibody fragment thereof, an aqueous carrier (e.g., water), trehalose (e.g., trehalose dehydrate), histidine (e.g., histidine/histidine-HCl), polysorbate 80, and EDTA. In certain embodiments, the composition or formulation comprises the components and quantities or concentrations set forth at Table 2.

In specific embodiments, the composition or formulation comprises or consists of about 18.7 mg/mL durvalumab, or antibody fragment thereof, about 12.5 mg/mL tremelimumab, or antibody fragment thereof, about 22 mM Histidine/Histidine-HCl, about 254 mM Trehalose dehydrate, about 0.17 mM EDTA, and about 0.02% w/v PS80 at a pH of about 5.8.

In specific embodiments, the composition or formulation comprises or consists of about 36.3 mg/mL durvalumab, or antibody fragment thereof, about 5.5 mg/mL tremelimumab, or antibody fragment thereof, about 24 mM Histidine/Histidine-HCl, about 260 mM Trehalose dehydrate, about 0.07 mM EDTA, and about 0.02% w/v PS80 at a pH of about 6.0.

In specific embodiments, the composition or formulation comprises or consists of about 40.0 mg/mL durvalumab, or antibody fragment thereof, about 4.0 mg/mL tremelimumab, or antibody fragment thereof, about 25 mM Histidine/Histidine-HCl, about 264 mM Trehalose dehydrate, about 0.05 mM EDTA, and about 0.02% w/v PS80 at a pH of about 6.0.

In specific embodiments, the composition or formulation comprises or consists of about 42.8 mg/mL durvalumab, or antibody fragment thereof, about 2.9 mg/mL tremelimumab, or antibody fragment thereof, about 25 mM Histidine/Histidine-HCl, about 267 mM Trehalose dehydrate, about 0.04 mM EDTA, and about 0.02% w/v PS80 at a pH of about 6.0.

In specific embodiments, the composition or formulation comprises or consists of about 44.4 mg/mL durvalumab, or antibody fragment thereof, about 2.2 mg/mL tremelimumab, or antibody fragment thereof, about 25 mM Histidine/Histidine-HCl, about 269 mM Trehalose dehydrate, about 0.03 mM EDTA, and about 0.02% w/v PS80 at a pH of about 6.0.

In certain embodiments, the formulations of the present disclosure exhibit stability at the temperature range of about 23° C. to about 27° C. or about 20° C. to about 24° C. for at least 6 months. Additionally or alternatively, in certain embodiments, the formulations are stable at the temperature range of about 2° C. to about 8° C. for at least 6 months, at least 1 year, or more. Additionally or alternatively, in certain embodiments, the formulations are stable at the temperature range of 38° C. to about 42° C. for at least 1 month and, in some embodiments, for at least 3 months.

Stability may be assessed, for example, by protein concentration determination (e.g., measuring absorbance at 280 mM or ion exchange titer chromatography) or high performance size exclusion chromatography (HPSEC). In certain embodiments, stability can be assessed by maintenance of a level of purity over time. For example, in certain embodiments, coformulations of the present disclosure have less than 1%, less than 0.8%, less than 0.75%, less than 0.7%, less than 0.6%, less than 0.5%, or even less than 0.4% decrease in purity/year when stored at about 2° C. to about 8° C., as determined by HPSEC. In one embodiment, formulations of the present disclosure have a shelf-life of greater than 6 months, or greater than 1 year, as determined by HPSEC, which monitors the presence or absence of fragments and/or aggregate species.

In certain embodiments, the coformulation compositions of the present disclosure promote low to undetectable levels of aggregation and/or fragmentation when stored under 2° C. to 8° C., after the storage for the defined periods as set forth above. Preferably, no more than 5%, no more than 4%, no more than 3%, no more than 2%, no more than 1%, and most preferably no more than 0.5% of the antibodies (including antibody fragments thereof) form fragment or aggregate (reversible or non-reversible) forms as measured by HPSEC, after the storage for the defined periods as set forth above. Aggregation and/or fragmentation assessed by various assays including, for example, one or more of visual inspection, flow microscopy, centrifugation gel electrophoresis (e.g., under reducing and non-reducing conditions), and ion exchange chromatography.

Furthermore, coformulation compositions of the present disclosure render almost no loss in biological activities of the antibody (including antibody fragment thereof) during the prolonged storage under the condition described above, as assessed by various assays. For example, immunological assays, such as enzyme-linked immunosorbent assay (ELISA) and radioimmunoas say can measure the ability of the antibody (including antibody fragment thereof) to immunospecifically bind to an antigen. Potency of the antibody components can be determined using any number of biological assays, for example, reporter gene bioassay methods specific for each antibody. The coformulation compositions of the present disclosure promote, after the storage for the above-defined periods, more than 80%, more than 85%, more than 90%, more than 95%, more than 98%, more than 99%, more than 99.5%, more than 99.8%, or more than 99.9% retention of the initial biological activities (e.g., the ability to bind to an antigen) of the formulation prior to the storage. In some embodiments, the coformulation compositions of the present disclosure promote, after the storage for the above-defined periods, at least 80%, at least 85%, at least 90%, at least 95%, at least 98%, at least 99%, at least 99.5%, at least 99.8%, or at least 99.9% retention of the biological activity compared to a reference antibody representing the antibody prior to the storage.

Therapeutic Methods

The coformulation compositions of the present disclosure are useful, including for example in the delivery and/or storage of pharmaceutical compositions. In one embodiment, the coformulation composition comprises a coformulation composition comprising an anti-PD-L1 antibody (e.g., durvalumab), or an antigen-binding fragment thereof, and an anti-CTLA-4 antibody (e.g., tremelimumab) or an antigen-binding fragment thereof. The combination of programmed cell death-1/programmed cell death ligand-1 (PD-1/PD-L1) pathway and cytotoxic T-lymphocyte-associated antigen-4 (CTLA-4) pathway blockade targets two compartments: anti-PD-L1/anti-PD-1 acts in the tumor microenvironment and blocks inhibition of T-cell function, whereas anti-CTLA-4 acts in the lymphoid compartment to expand the number and repertoire of tumor-reactive T cells.[1,2]

Durvalumab (MEDI4736) is a selective, high-affinity human IgG1 monoclonal antibody (mAb) that blocks PD-L1 binding to PD-1 and CD80[4] but does not bind to programmed-cell death (PD-L2),[5] avoiding potential immune-related toxicity due to PD-L2 blockade that is observed in susceptible animal models.[6,7] In an ongoing Phase ½ study, durvalumab monotherapy has produced durable responses in patients with advanced NSCLC, with a manageable tolerability profile; confirmed/unconfirmed ORR with durvalumab 10 mg/kg every 2 weeks (q2w) was 27% in PD-L1+ patients, and 5% in PD-L1− patients.[8] In that study, a maximum tolerated dose (MTD) was not reached in the dose-escalation phase, and dose-expansion cohorts were initiated using a dose of 10 mg/kg q2w.[8] Tremelimumab (CP-675,206) is a selective human IgG2 mAb inhibitor of CTLA-4[9]; it promotes T cell activity through CTLA-4 inhibition, but does not appear to directly deplete regulatory T cells.[10] The combination of durvalumab and tremelimumab was based on strong preclinical data indicating that the two pathways are non-redundant, which suggests that targeting both may have additive or synergistic effects.[11]

By "Durvalumab" (also known as "MEDI4736") is meant an antibody or antigen binding fragment thereof that selectively binds a PD-L1 polypeptide and comprises at least a portion of a light chain variable region comprising the amino acid sequence of SEQ ID NO: 1 and/or at least a portion of a heavy chain variable region comprising the amino acid sequence of SEQ ID NO: 2.

Information regarding durvalumab (or antigen-binding fragments thereof) for use in the methods provided herein can be found in U.S. Pat. No. 8,779,108, the disclosure of which is incorporated herein by reference in its entirety. The fragment crystallizable (Fc) domain of durvalumab contains a triple mutation in the constant domain of the IgG1 heavy chain that reduces binding to the complement component C lq and the Fcγ receptors responsible for mediating antibody-dependent cell-mediated cytotoxicity (ADCC). Durvalumab is selective for PD-L1 and blocks the binding of PD-L1 to the PD-1 and CD80 receptors. Durvalumab can relieve PD-L1-mediated suppression of human T-cell activation in vitro and inhibits tumor growth in a xenograft model via a T-cell dependent mechanism.

Durvalumab comprises a heavy chain and a light chain or a heavy chain variable region and a light chain variable region. In a specific aspect, durvalumab or an antigen-binding fragment thereof for use in the methods provided herein comprises a light chain variable region comprising the amino acid sequence of SEQ ID NO: 1 and a heavy chain variable region comprising the amino acid sequence of SEQ ID NO: 2. In a specific aspect, durvalumab or an antigen-binding fragment thereof for use in the methods provided herein comprises a heavy chain variable region and a light chain variable region, wherein the heavy chain variable region comprises the Kabat-defined CDR1, CDR2, and CDR3 sequences of SEQ ID NOs: 3-5, and wherein the light chain variable region comprises the Kabat-defined CDR1, CDR2, and CDR3 sequences of SEQ ID NOs: 6-8. Those of ordinary skill in the art would easily be able to identify Chothia-defined, Abm-defined or other CDR definitions known to those of ordinary skill in the art. In a specific aspect, durvalumab or an antigen-binding fragment thereof for use in the methods provided herein comprises the variable heavy chain and variable light chain CDR sequences of the 2.14H9OPT antibody as disclosed in U.S. Pat. No. 8,779,108, which is herein incorporated by reference in its entirety.

By "Tremelimumab" is meant an antibody or antigen binding fragment thereof that selectively binds a CTLA-4 polypeptide and comprises at least a portion of a light chain variable region comprising the amino acid sequence of SEQ ID NO: 9 and/or at least a portion of a heavy chain variable region comprising the amino acid sequence of SEQ ID NO: 10. Exemplary anti-CTLA-4 antibodies are described for example at U.S. Pat. Nos. 6,682,736; 7,109,003; 7,123,281; 7,411,057; 7,824,679; 8,143,379; 7,807,797; and 8,491,895 (Tremelimumab is 11.2.1, therein), which are herein incorporated by reference. Tremelimumab is an exemplary anti-CTLA-4 antibody. Tremelimumab sequences are provided in the sequence listing below.

Information regarding tremelimumab (or antigen-binding fragments thereof) for use in the methods provided herein can be found in U.S. Pat. No. 6,682,736 (where it is referred to as 11.2.1, the disclosure of which is incorporated herein by reference in its entirety. Tremelimumab (also known as CP-675,206, CP-675, CP-675206, and ticilimumab) is a human IgG2 monoclonal antibody that is highly selective for CTLA-4 and blocks binding of CTLA-4 to CD80 (B7.1) and CD86 (B7.2). It has been shown to result in immune activation in vitro and some patients treated with tremelimumab have shown tumor regression.

Tremelimumab and antigen-binding fragments thereof for use in the methods provided herein comprises a heavy chain and a light chain or a heavy chain variable region and a light chain variable region. In a specific aspect, tremelimumab or an antigen-binding fragment thereof for use in the methods provided herein comprises a light chain variable region comprising the amino acid sequence of SEQ ID NO: 9 and a heavy chain variable region comprising the amino acid sequence of SEQ ID NO: 10. In a specific aspect, tremelimumab or an antigen-binding fragment thereof for use in the methods provided herein comprises a heavy chain variable region and a light chain variable region, wherein the heavy chain variable region comprises the Kabat-defined CDR1, CDR2, and CDR3 sequences of SEQ ID NOs: 11-13, and wherein the light chain variable region comprises the Kabat-defined CDR1, CDR2, and CDR3 sequences of SEQ ID NOs: 14-16. Those of ordinary skill in the art would easily be able to identify Chothia-defined, Abm-defined or other CDR definitions known to those of ordinary skill in the art. In a specific aspect, tremelimumab or an antigen-binding fragment thereof for use in the methods provided herein comprises or the variable heavy chain and variable light chain CDR sequences of the 11.2.1 antibody as disclosed in U.S. Pat. No. 6,682,736, which is herein incorporated by reference in its entirety.

The term "antigen binding fragment" refers to a portion of an intact antibody and/or refers to the antigenic determining variable regions of an intact antibody. It is known that the antigen binding function of an antibody can be performed by fragments of a full-length antibody. Examples of antibody fragments include, but are not limited to, Fab, Fab', F(ab')2, and Fv fragments, linear antibodies, single chain antibodies, diabodies, and multispecific antibodies formed from antibody fragments.

In certain aspects, a patient presenting with a solid tumor (e.g., NSCLC) is administered a coformulation composition comprising durvalumab, or an antigen-binding fragment thereof, and tremelimumab, or an antigen-binding fragment thereof. The amount of a coformulation composition comprising durvalumab, or an antigen-binding fragment thereof, and tremelimumab, or an antigen-binding fragment thereof, to be administered to the patient will depend on various parameters such as the patient's age, weight, clinical assessment, tumor burden and/or other factors, including the judgment of the attending physician.

The coformulation composition of the invention can be administered only once or infrequently while still providing benefit to the patient. In further aspects the patient is administered additional follow-on doses. Follow-on doses can be administered at various time intervals depending on the patient's age, weight, clinical assessment, tumor burden, and/or other factors, including the judgment of the attending physician.

In certain aspects the patient is administered one or more doses (e.g., two, three, or more doses) of a coformulation composition comprising durvalumab or an antigen-binding fragment thereof and tremelimumab or an antigen-binding fragment thereof. By "multidose" is meant two or more doses. In particular, a multidose formulation is administered in 2, 3, 4, 5, 6, 7, 8, 9, 10 or a plurality of doses.

The intervals between doses of a coformulation composition comprising durvalumab, or an antigen-binding fragment thereof, and tremelimumab, or an antigen-binding fragment thereof, can be every four weeks. The intervals between doses of a coformulation composition comprising durvalumab, or an antigen-binding fragment thereof, and tremelimumab, or an antigen-binding fragment thereof, can be every twelve weeks. The intervals between doses of a coformulation composition comprising durvalumab, or an antigen-binding fragment thereof, and tremelimumab, or an antigen-binding fragment thereof can be every four weeks for six cycles and then every twelve weeks.

In some embodiments, at least two doses of a coformulation composition comprising durvalumab, or an antigen-binding fragment thereof, and tremelimumab, or an antigen-binding fragment thereof, are administered to the patient. In some embodiments, at least three doses, at least four doses, at least five doses, at least six doses, at least seven doses, at least eight doses, at least nine doses, at least ten doses, or at least fifteen doses or more can be administered to the patient. In some embodiments, a coformulation composition comprising durvalumab, or an antigen-binding fragment thereof, and tremelimumab, or an antigen-binding fragment thereof, is administered over a four-week treatment period, over an eight-week treatment period, over a sixteen-week treatment period, over a twenty-week treatment period, over a twenty-four-week treatment period, or over a one-year or more treatment period.

In certain aspects, administration of a coformulation composition comprising durvalumab, or an antigen-binding fragment thereof, and tremelimumab or an antigen-binding fragment thereof, according to the methods provided herein is through parenteral administration. For example, a coformulation composition comprising durvalumab or an antigen-binding fragment thereof and tremelimumab or an antigen-binding fragment thereof, can be administered by intravenous infusion or by subcutaneous injection. In certain embodiments, the administration is by intravenous infusion.

Co-therapy

Treatment of a patient with a solid tumor using a coformulation composition of the invention, comprising an anti-CTLA-4 antibody and an anti-PD-L1 antibody, or antigen-binding fragments thereof, as provided herein can result in an additive or synergistic effect. As used herein, the term "synergistic" refers to a combination of therapies (e.g., a combination of anti-CTLA-4 antibody and anti-PD-L1 antibody, or antigen binding fragments thereof).

A synergistic effect of a combination of therapies (e.g., a combination of anti-CTLA-4 antibody and anti-PD-L1 antibody, or antigen binding fragments thereof) permits the use of lower dosages of one or more of the therapeutic agents and/or less frequent administration of said therapeutic agents to a patient with a solid tumor. The ability to utilize lower dosages of therapeutic agents and/or to administer said therapies less frequently reduces the toxicity associated with the administration of said therapies to a subject without reducing the efficacy of said therapies in the treatment of a solid tumor. In addition, a synergistic effect can result in improved efficacy of therapeutic agents in the management, treatment, or amelioration of a solid tumor. The synergistic effect of a combination of therapeutic agents can avoid or reduce adverse or unwanted side effects associated with the use of either single therapy.

In co-therapy, a combination of anti-CTLA-4 antibody and anti-PD-L1 antibody, or antigen binding fragments thereof, can be included in the same pharmaceutical composition (e.g., a coformulation). In certain aspects, pharmaceutical compositions in accordance with the present disclosure comprise a pharmaceutically acceptable, non-toxic, sterile carrier such as physiological saline, non-toxic buffers, preservatives and the like. Suitable formulations are disclosed herein for use in the treatment methods.

Assays for Measuring Tumor Response

The methods of treatment provided herein can decrease, retard or stabilize tumor growth. In some aspects the reduction or retardation can be statistically significant. A reduction in tumor growth can be measured by comparison to the growth of patient's tumor at baseline, against an expected tumor growth, against an expected tumor growth based on a large patient population, or against the tumor growth of a control population. In certain aspects, a tumor response is measured using the Response Evaluation Criteria in Solid Tumors (RECIST).

In certain aspects, a tumor response is detectable after administration of two or more doses of a coformulation composition comprising durvalumab or an antigen-binding fragment thereof and tremelimumab or an antigen-binding fragment thereof. In certain aspects, a tumor response is detectable at week 8. In certain aspects, a tumor response is detectable at week 33. In certain aspects, a tumor response is detectable at week 50.

In certain aspects "objective response" (regarding antitumor activity) is defined as confirmed complete or partial response (CR or PR). In certain aspects "disease control" at 24 weeks is defined as CR, PR, or stable disease (SD) duration of ≥24 weeks. The objective response rate (ORR) and disease control rate (DCR) at 24 weeks are estimated and 95% confidence intervals (CIs) are calculated using the exact binomial distribution.

In certain aspects, a patient achieves disease control (DC). Disease control can be a complete response (CR), partial response (PR), or stable disease (SD).

A "complete response" (CR), a "partial response" (PR), and "stable disease" (SD) can be determined as defined in Table 1 below.

TABLE 1

Evaluation of Overall Response

| Target Lesions | Non-target lesions | New Lesions | Overall Response |
|---|---|---|---|
| Complete Response | Complete Response | No | Complete Response |
| No target lesion[a] | Complete Response | No | Complete Response |
| Complete Response | Not evaluable[b] | No | Partial Response |
| Complete Response | Non-complete response/non-progressive disease | No | Partial Response |
| Partial Response | Non-progressive disease and not evaluable[b] | No | Partial Response |
| Stable Disease | Non-progressive disease and not evaluable[b] | No | Stable Disease |
| Not all evaluated | Non-progressive disease | No | Not evaluable |
| No target lesion[a] | Not all evaluated | No | Not evaluable |
| No target lesion[a] | Non-complete response/non-progressive disease | No | Non-complete response/non-progressive disease |
| Progressive Disease | Any | Yes or No | Progressive Disease |
| Any | Progressive Disease | Yes or No | Progressive Disease |
| Any | Any | Yes | Progressive Disease |
| No target lesion[a] | Unequivocal progressive disease | Yes or No | Progressive Disease |
| No target lesion[a] | Any | Yes | Progressive Disease |

[a]Defined as no target lesions at baseline.
[b]Not evaluable is defined as either when no or only a subset of lesion measurements are made at an assessment.

In certain aspects, administration of a coformulation composition comprising durvalumab, or an antigen-binding fragment thereof, and tremelimumab, or an antigen-binding fragment thereof can increase progression-free survival (PFS).

In certain aspects, administration of coformulation composition comprising durvalumab, or an antigen-binding fragment thereof, and tremelimumab, or an antigen-binding fragment thereof can increase overall survival (OS).

In some embodiments, the patient has previously received treatment with at least one chemotherapeutic agent. In some embodiments, the patient has previously received treatment with at least two chemotherapeutic agents. The chemotherapeutic agent can be, for example, and without limitation, Vemurafenib, Erlotinib, Afatinib, Cetuximab, Carboplatin, Bevacizumab, Erlotinib, Gefitinib, and/or Pemetrexed.

In some embodiments, the NSCLC is refractory or resistant to at least one chemotherapeutic agent. In some embodiments, the tumor is refractory or resistant to at least two chemotherapeutic agents. The tumor can be refractory or resistant to one or more of, for example, and without limitation, Vemurafenib, Erlotinib, Afatinib, Cetuximab, Carboplatin, Bevacizumab, Erlotinib, Gefitinib, and/or Pemetrexed. In some embodiments, the NSCLC is negative for PD-L1. In some embodiments, the NSCLC is positive for PD-L1.

In some embodiments, the patient has an Eastern Cooperative Oncology Group (ECOG) (Oken M M, et al. *Am. J. Clin. Oncol.* 5: 649-55 (1982)) performance status of 0 or 1 prior to the administration of a coformulation composition comprising durvalumab, or an antigen-binding fragment thereof, and tremelimumab, or an antigen-binding fragment thereof.

According to the methods provided herein, administration of a coformulation composition comprising durvalumab, or an antigen-binding fragment thereof, and tremelimumab, or an antigen-binding fragment thereof, can result in desirable pharmacokinetic parameters. Total drug exposure can be estimated using the "area under the curve" (AUC). "AUC (tau)" refers to AUC from time 0 to time τ, the dosing interval, whereas "AUC (inf)" refers to the AUC until infinite time. The administration can produce AUC (tau) of about 600 to about 3,000μg/mL*day of durvalumab or antigen-binding fragment thereof and about 250 to about 350 μg/mL*day of tremelimumab or antigen-binding fragment thereof. The administration can produce a maximum observed concentration (Cmax) of about 60 to about 300 μg/mL durvalumab or antigen-binding fragment thereof and of about 25 to about 35 μg/mL tremelimumab or antigen-binding fragment thereof. The administration can produce a C trough (minimum plasma drug concentration) of about 5 to about 40 μg/mL durvalumab or antigen-binding fragment thereof and about 4 to about 6 μg/mL tremelimumab or antigen-binding fragment thereof.

As provided herein, durvalumab or an antigen-binding fragment thereof in a coformulation composition comprising durvalumab, or an antigen-binding fragment thereof, and tremelimumab, or an antigen-binding fragment thereof, can also decrease free (soluble) PD-L1 levels. Free (soluble) PD-L1 refers to PD-L1 that is not bound (e.g., by durvalumab). In some embodiments, PD-L1 levels are reduced by at least 65%. In some embodiments, PD-L1 levels are reduced by at least 80%. In some embodiments, PD-L1 levels are reduced by at least 90%. In some embodiments, PD-L1 levels are reduced by at least 95%. In some embodiments, PD-L1 levels are reduced by at least 99%. In some embodiments, PD-L1 levels are not detectable following administration of a coformulation composition comprising durvalumab, or an antigen-binding fragment thereof, and tremelimumab, or an antigen-binding fragment thereof.

In some embodiments, PD-L1 levels are reduced by at least 65% after one or more administrations of a coformulation composition comprising durvalumab, or an antigen-binding fragment thereof, and tremelimumab, or an antigen-binding fragment thereof. In some embodiments, PD-L1 levels are reduced by at least 80% after a single administration of a coformulation composition comprising durvalumab, or an antigen-binding fragment thereof, and tremelimumab, or an antigen-binding fragment thereof. In some embodiments, PD-L1 levels are reduced by at least 90% after a single administration of a coformulation composition comprising durvalumab, or an antigen-binding fragment thereof, and tremelimumab, or an antigen-binding fragment thereof. In some embodiments, PD-L1 levels are reduced by at least 95% after a single administration of a coformulation composition comprising durvalumab, or an antigen-binding fragment thereof, and tremelimumab, or an antigen-binding fragment thereof. In some embodiments, PD-L1 levels are reduced by at least 99% after a single administration of a coformulation composition comprising durvalumab, or an antigen-binding fragment thereof, and tremelimumab, or an antigen-binding fragment thereof. In some embodiments, PD-L1 levels are not detectable following a single administration of a coformulation composition comprising durvalumab, or an antigen-binding fragment thereof, and tremelimumab, or an antigen-binding fragment thereof.

Provided herein are methods for treating solid tumor non-small cell lung cancer (NSCLC) using a coformulation composition comprising durvalumab, or an antigen-binding fragment thereof, and tremelimumab, or an antigen-binding fragment thereof. A combination of durvalumab and tremelimumab is effective at treating non-small cell lung cancers. The invention is based at least in part on these discoveries. The methods provided include administering an effective amount of durvalumab, or an antigen-binding fragment thereof, and tremelimumab, or an antigen-binding fragment thereof, as a coformulation composition to treat non-small cell lung cancer (NSCLC).

There are three main subtypes of NSCLC: squamous cell carcinoma, adenocarcinoma, and large cell (undifferentiated) carcinoma. Other subtypes include adenosquamous carcinoma and sarcomatoid carcinoma. NSCLC may comprise a mutation in KRAS or in the Epidermal Growth Factor receptor. Such mutations are known in the art and described, for example, by Riely et al., Proc Am Thorac Soc. 2009 Apr 15;6(2):201-5, which is incorporated herein by reference.

Subjects suffering from lung cancer (e.g., non-small cell lung cancer) may be tested for PD-L1 polynucleotide or polypeptide expression in the course of selecting a treatment method. Patients identified as having tumors that are negative for PD-L1 (e.g., as defined by Ct or IHC-M score) or by having reduced or undetectable levels of PD-L1 relative to a reference level are identified as responsive to treatment with a combination of an anti-PD-L1 antibody and tremelimumab. Such patients are administered durvalumab, or an antigen-binding fragment thereof in combination with tremelimumab or an antigen-binding fragment thereof.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the coformulations compositions and therapeutic methods of the invention, and are not intended to limit the scope of what the inventors regard as their invention.

EXAMPLES

Example 1

Durvalumab and Tremelimumab Coformulation Stability Assessment

Materials

All materials used for the study were of USP or Multi-compendial grade. All solutions and buffers were prepared using USP or HPLC water and were filtered through 0.2 μm PVDF filters (Millipore, Millex GV, SLGO33RB) before further use. An anti-PD-L1 antibody (durvalumab) and an anti-CTLA-4 antibody (tremelimumab) of high purities produced by MedImmune (Gaithersburg, MD) were used in this study. All samples were prepared under sterile aseptic conditions in the Biosafety Cabinet Hood (BSC).

Methods and results

Selected time points were evaluated for flow microscopy (Microflow Imager™) bioanalyzer, Ion exchange chromatography (IEC), and potency as appropriate.

Visual Appearance

The visual appearance of samples in 3 cc, 13mm glass vials was assessed for visible particles, clarity/opalescence, and color at a visual inspection station following procedures adapted from the Ph. Eur. (sections 2.9.20, 2.2.1 and 2.2.2 respectively). Sub-visible particle (SVP) counts were measured by flow microscopy using a Microflow Imager™, MFI™ (Proteinsimple, Ontario, Canada). To distinguish irregular subvisible proteinaceous particles from spherical air bubbles, a software aspect ratio less or equal to 0.85 was used to process the raw counts.

Upon mixing at different durvalumab to tremelimumab concentration ratios, the final excipient concentrations and pH varied. The final formulation compositions of various conformations at different concentration ratios are shown at Table 2.

The stability of coformulated samples at different durvalumab to tremelimumab concentration ratios was assessed and compared to those of durvalumab alone or tremelimumab alone. Over the course of the study, no apparent visible particle formation was observed for any stability studies.

Figure 2:
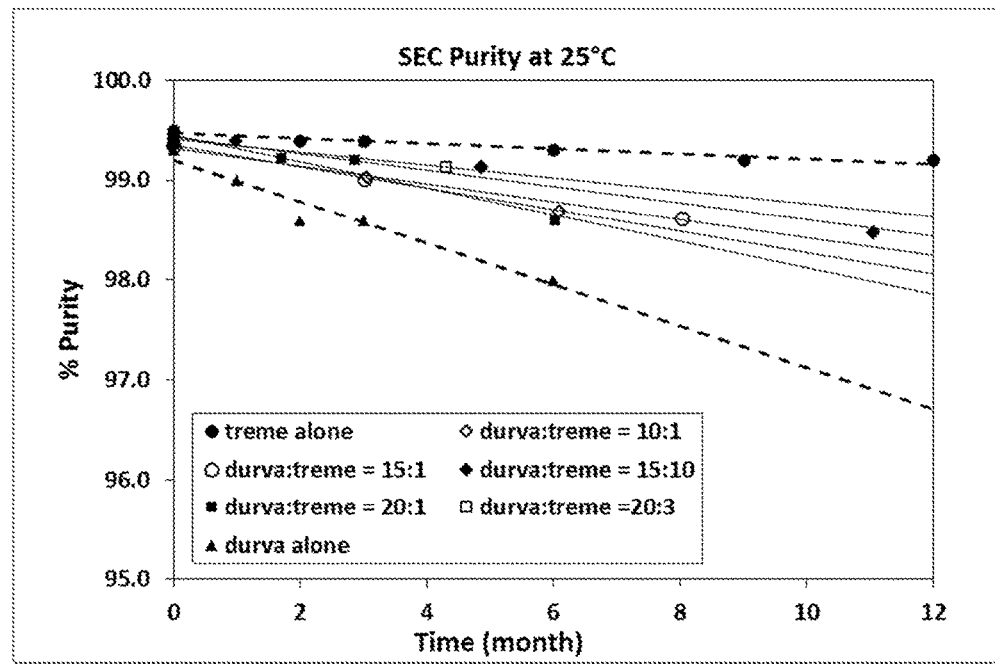
FIG. 2 is a graph depicting purity of coformulated durvalumab/tremelimumab as assessed by HPSEC at various concentration ratios when compared to durvalumab alone or tremelimumab alone at 25° C.
Figure 3:
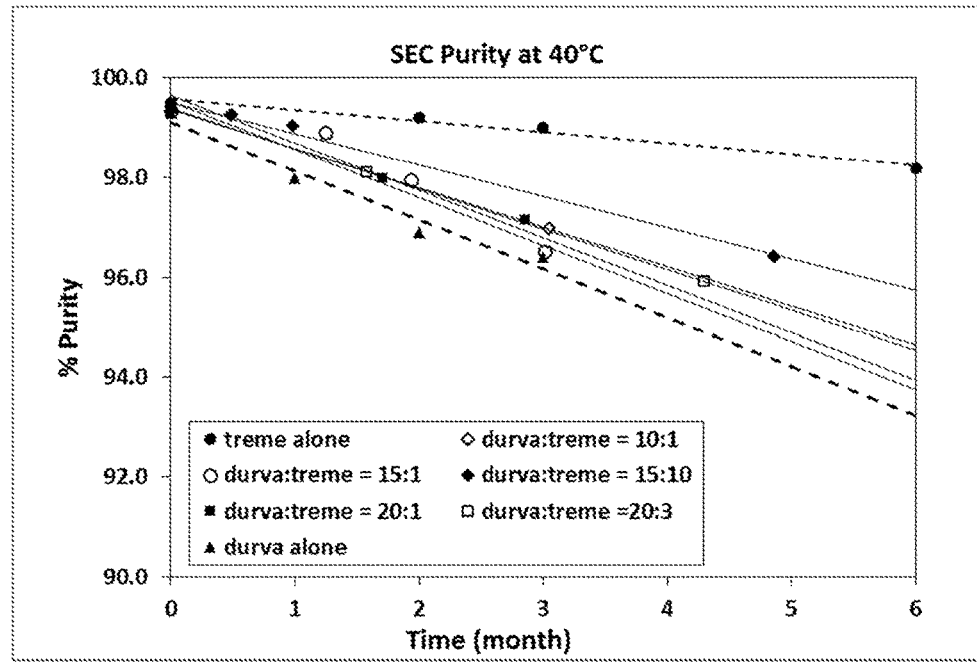
FIG. 3 is a graph depicting purity of coformulated durvalumab/tremelimumab as assessed by HPSEC at various concentration ratios when compared to durvalumab alone or tremelimumab alone at 40° C.
Figure 4:
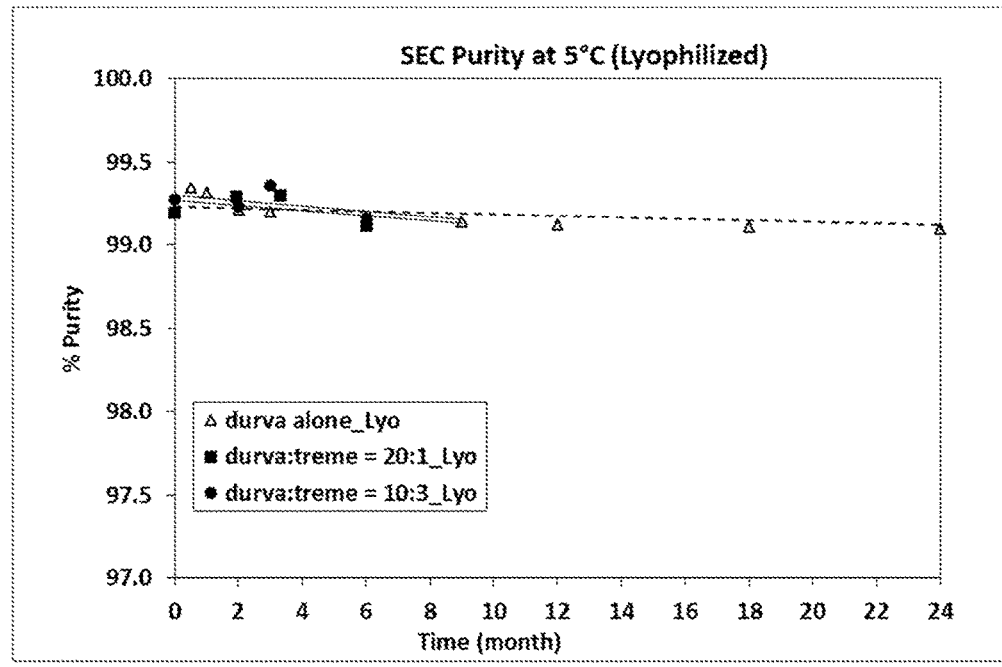
FIG. 4 is a graph depicting purity of coformulated lyophilized durvalumab/tremelimumab as assessed by high performance size exclusion chromatography (HPSEC) at various concentration ratios when compared to lyophilized durvalumab alone at 5° C.
Figure 5:
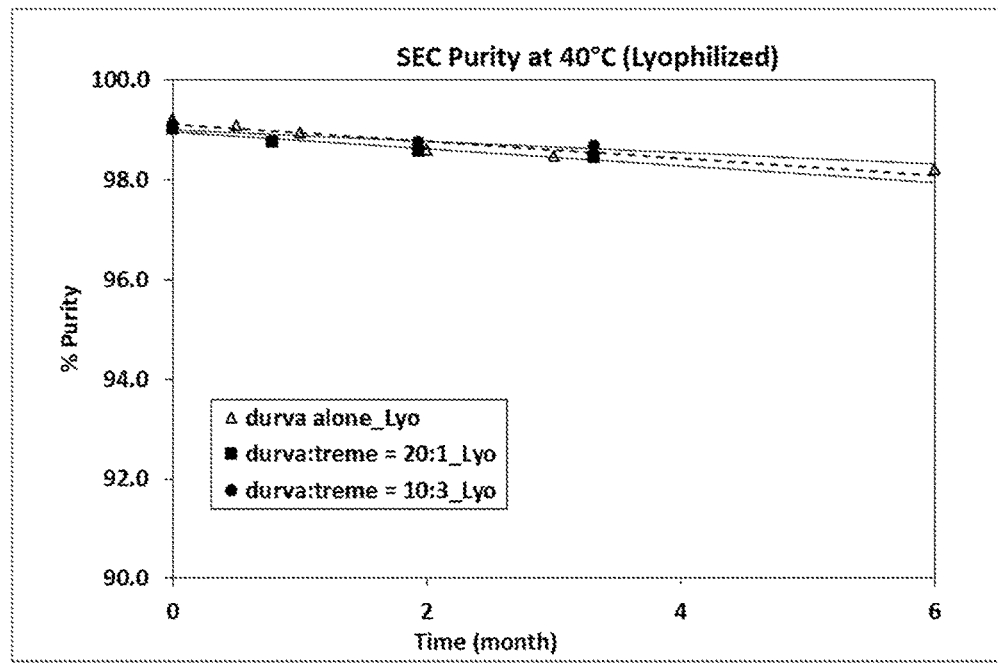
FIG. 5 is a graph depicting purity of coformulated lyophilized durvalumab/tremelimumab as assessed by high performance size exclusion chromatography (HPSEC) at various concentration ratios when compared to lyophilized durvalumab alone at 40° C.
Figure 6:
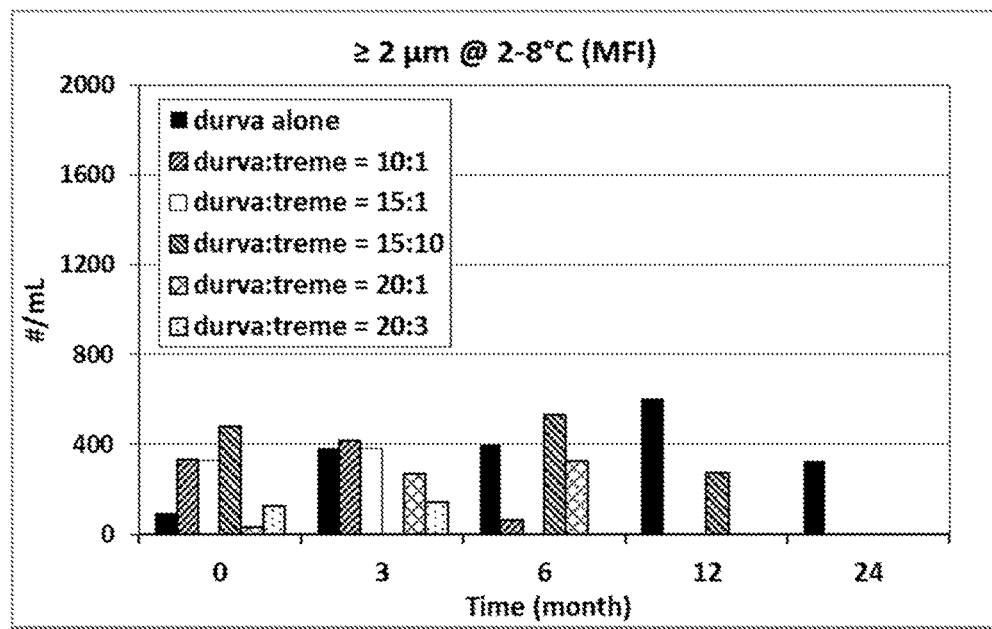
FIG. 6 is a bar graph depicting ≥2μm sub-visible particle formation of coformulated durvalumab/tremelimumab at different concentration ratios when compared to durvalumab alone by flow microscopy (Microflow Imager™; Proteinsimple, Ontario, Canada) at 5° C.
Figure 7:
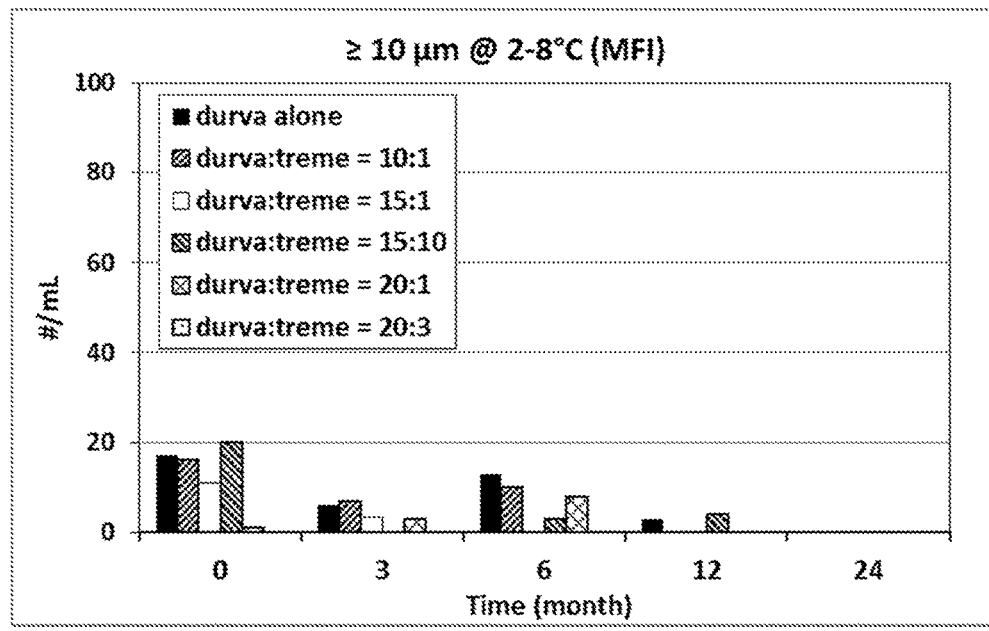
FIG. 7 is a bar graph depicting ≥10 μm sub-visible particle formation of coformulated durvalumab/tremelimumab at different concentration ratios when compared to durvalumab alone by flow microscopy (Microflow Imager™) at 5° C.
Figure 8:
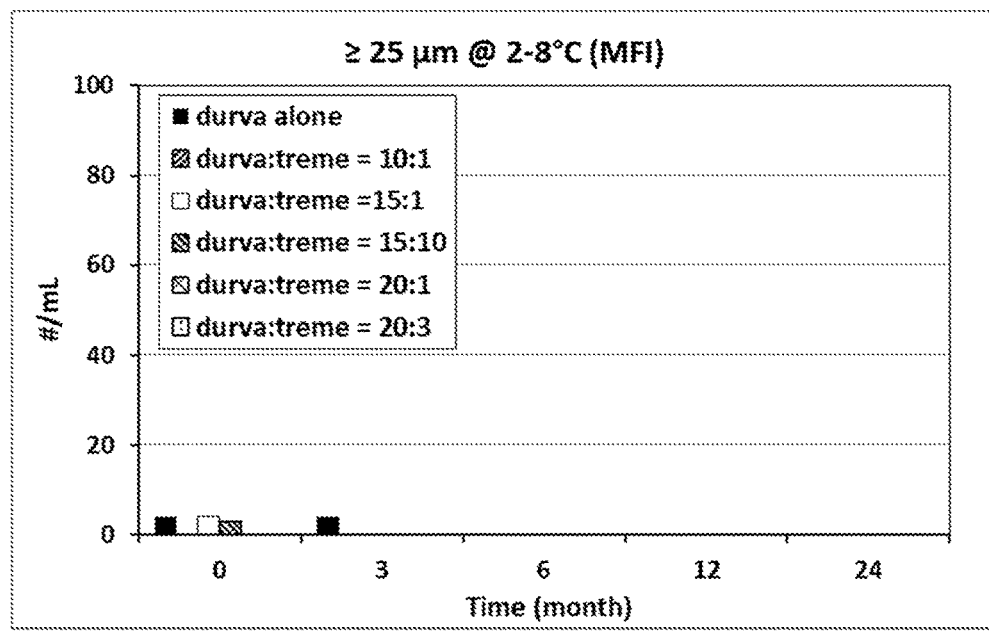
FIG. 8 is a bar graph depicting ≥25 μm sub-visible particle formation of coformulated durvalumab/tremelimumab at different concentration ratios when compared to durvalumab alone by flow microscopy (Microflow Imager™) at 5° C.
Figure 9:
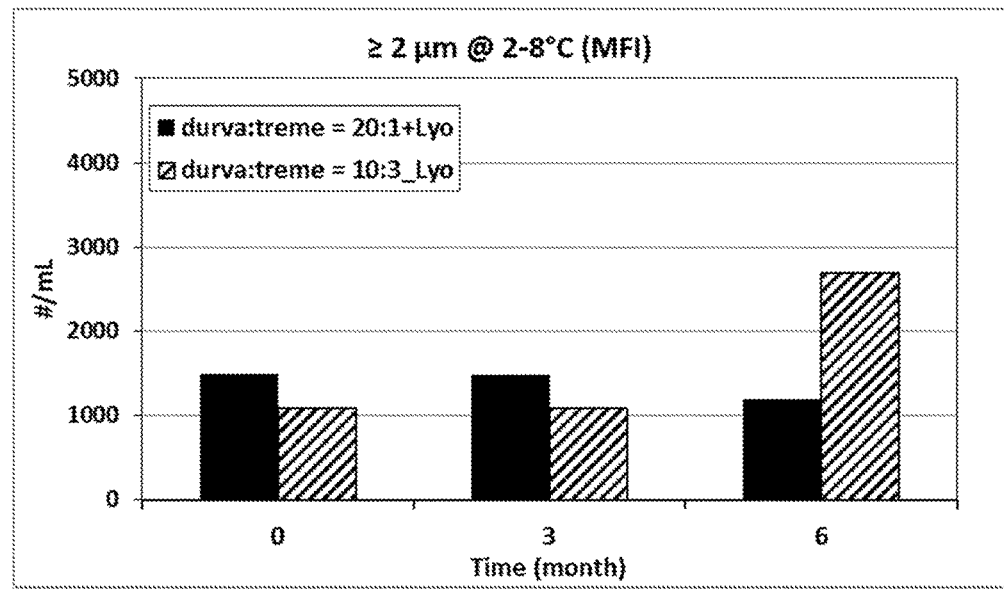
FIG. 9 is a bar graph depicting ≥2 μm sub-visible particle formation of coformulated lyophilized durvalumab/tremelimumab after reconstitution at 10:3 or 20:1 concentration ratios when compared to durvalumab alone by flow microscopy (Microflow Imager™; Proteinsimple, Ontario, Canada) at 5° C.
Figure 10:
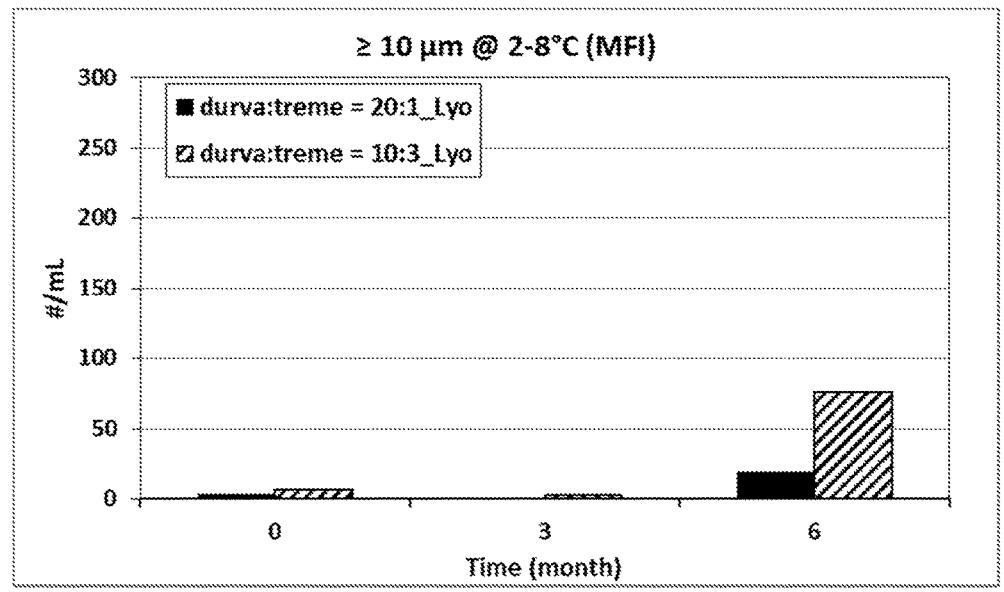
FIG. 10 is a bar graph depicting ≥10 μm sub-visible particle formation of coformulated lyophilized durvalumab/tremelimumab after reconstitution at 10:3 or 20:1 concentration ratios when compared to durvalumab alone by flow microscopy (Microflow Imager™; Proteinsimple, Ontario, Canada) at 5° C.
Figure 11:
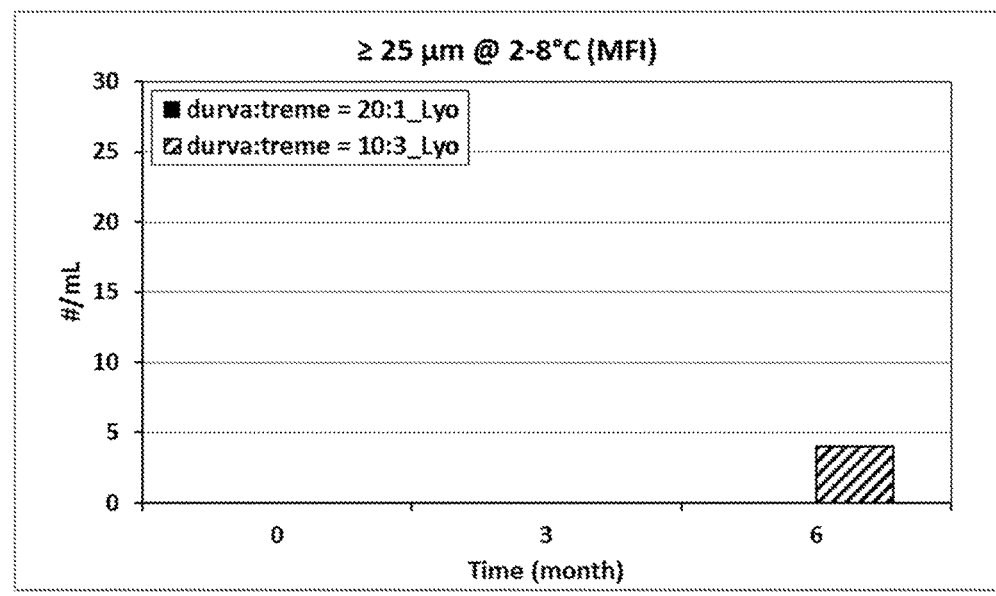
FIG. 11 is a bar graph depicting >25 μm sub-visible particle formation of coformulated lyophilized durvalumab/tremelimumab after reconstitution at 10:3 or 20:1 concentration ratios when compared to durvalumab alone by flow microscopy (Microflow Imager™; Proteinsimple, Ontario, Canada) at 5° C.

FIGS. 1-5 illustrate the purity loss rates of coformulations at different durvalumab to tremelimumab concentration ratios when compared to durvalumab alone or tremelimumab alone at 5, 25, or 40° C. As shown in the figures, the purity loss rates of coformulated samples were similar to that of durvalumab alone or tremelimumab alone (FIGS. 1-3 show aqueous formulations and FIGS. 4 and 5 show lyophilized formulations).

FIGS. 6-11 demonstrate the sub-visible particle counts of coformulated samples at different durvalumab to tremelimumab concentration ratios when compared to durvalumab alone under 2-8° C. incubation. Sub-visible particle (SVP) was measured by Microflow Imager™ (MFI™). Overall, no significant increases in SVP counts were detected for all samples.

mumab. Coformulated samples were injected onto an ion-exchange column at ambient column temperature and eluted with a salt gradient. Protein concentrations were determined by measuring absorbance at 280 mM with a spectrophotometer (Agilent UV-Vis spectrophotometer). Measured extinction coefficients of 1.52 $(mg/mL)^{-1} cm^{-1}$ and 1.43 $(mg/mL)^{-1} cm^{-1}$ were used to calculate protein concentrations for durvalumab and tremelimumab, respectively. For coformulation concentrations, a calculated extinction coefficient was derived based on the protein concentration ratio as shown at Table 3.

TABLE 3

| | Concentration ratio of durvalumab to tremelimumab | | | | |
|---|---|---|---|---|---|
| | 10:1 | 15:1 | 15:10 | 20:1 | 20:3 |
| Calculated extinction coefficient ($[mg/mL]^{-1}cm^{-1}$) | 1.51 | 1.51 | 1.48 | 1.52 | 1.51 |

TABLE 2

Formulation composition of different durvalumab and tremelimumab coformulations varied based on the protein concentration ratios.

| | durva alone | durva | treme | durva | treme | durva | treme | durva | treme | durva | treme | treme alone |
|---|---|---|---|---|---|---|---|---|---|---|---|---|
| Target concentration ratio | NA | 10 | 1 | 15 | 1 | 15 | 10 | 20 | 1 | 20 | 3 | NA |
| Actual protein concentration (mg/mL) | 50 | 40.0 | 4.0 | 42.8 | 2.9 | 18.7 | 12.5 | 44.4 | 2.2 | 36.3 | 5.5 | 20 |
| Total protein concentration of coformulation (mg/mL) | NA | 44.0 | | 45.7 | | 31.2 | | 46.6 | | 41.8 | | NA |
| Histidine/Histidine-HCl (mM) | 26 | 25 | | 25 | | 22 | | 25 | | 24 | | 20 |
| Trehalose dihydrate (mM) | 275 | 264 | | 267 | | 254 | | 269 | | 260 | | 222 |
| EDTA (mM) | 0 | 0.05 | | 0.04 | | 0.17 | | 0.03 | | 0.07 | | 0.27 |
| PS80 (%[w/v]) | 0.02 | 0.02 | | 0.02 | | 0.02 | | 0.02 | | 0.02 | | 0.02 |
| pH | 6.0 | 6.0 | | 6.0 | | 5.8 | | 6.0 | | 6.0 | | 5.5 |

Purity Determination by Size Exclusion Chromatography

Protein purity was measured by high performance size exclusion Chromatography (HPSEC) using a TSK-GEL G3000SWXL column (Tosoh Bioscience LLC, Mongomeryville, Pa.) with UV detection at 280 nm. A flow rate of 1.0 mL/min for 20 minutes using a pH 6.8 mobile phase containing 0.1 M sodium phosphate, 0.1 M sodium sulfate, and 0.05% (w/v) sodium azide was used to assay the samples.

Formulation Stability Studies

As described above, a series of coformulated durvalumab and tremelimumab mixtures were filled into clear glass vials (3 cc, 13 mm). For accelerated screening, samples were placed on stability at 40° C./75% RH. For longer-term stability studies, in addition to the accelerated 40° C. condition, studies were also performed at 25° C./60% RH and 2-8° C. The vials were visually inspected for visual appearance and samples were analyzed by HPSEC.

Protein Concentration Determination by Ion-exchange chromatography (IEC_concentration)

Ion exchange titer chromatography was used to quantify protein concentration and ratio of durvalumab and tremeli- Charge Isoforms Determination by Ion Exchange Chromatography (IEC)

Ion exchange chromatography (IEC) was used to measure charge isoforms, specifically charge heterogeneity of tremelimumab. Coformulated samples were injected onto an ion-exchange column at ambient column temperature and eluted with a salt gradient. Eluted protein was detected using UV absorbance at 220 nm. Results were reported with respect to % area of and pre-peak (acidic variants), main peak, and post-peak (basic variants) for each component in the co-formulation.

Reducing and Non-reducing Gel Electrophoresis

Fragmentation was determined by gel electrophoresis under denaturing, non-reducing and denaturing, reducing conditions. Prior to analysis, test samples were adjusted to the same concentration and mixed with SDS denaturing sample buffer in the presence of dithiothreitol (reducing) or N-ethylmaleimide (non-reducing; samples were denatured and alkylated). For analysis under reducing conditions, samples were denatured and reduced to their heavy chain and light chain species. The alkylated or reduced samples were loaded on a chip filled with a sieving polymer and fluorescence dye. The charged protein species are electrophoretically driven by a voltage gradient. Due to a constant mass-to-charge ratio and the presence of a sieving polymer matrix, the charged protein species are separated by size. The protein-dye complexes were detected by laser-induced fluorescence. Data were translated into electropherograms and peak areas quantified to determine purity and fragmentation levels. Results for reducing gel electrophoresis are reported as peak area percentage of the heavy chain plus the light chain and percent impurities. Results for non-reducing gel electrophoresis are reported as percent major peak and percent fragment.

To determine the purity and relative fragmentation of the main peak of coformulated Durvalumab/Tremelimumab at 20:1 ratio, coformulated material was stored at 5° C., 25° C., and 40° C. for twelve months. FIGS. 15-20 demonstrate the fragmentation profile of coformulation durvalumab and tremelimumab at 20:1 ratio when compared to durvalumab or tremelimumab alone. At various time points the purity of the main peak of coformulated material, Durvalumab alone, and Tremelimumb alone were assessed by reducing (FIGS. 15-17) and non-reducing (FIGS. 18-20) gel electrophoresis to evaluate the level of fragmentation. As shown in the figures, the coformulated material displayed similar percent purity as each antibody alone. As a further assessment of purity, the protein concentrations of the main peak of coformulated Durvalumab/Tremelimumab 20:1 ratio, Durvalumab alone, and Tremelimumab alone were measured by A280 and ion exchange titer chromatography after incubation at 2° C. to 8° C. for up to six months (Table 4). The results indicated the fragment formation in the coformulation was similar to that of durvalumab alone or tremelimumab alone.

TABLE 4

| Protein Concentration | | Time (months) | | |
|---|---|---|---|---|
| | | 0 | 3 | 6 |
| A280 (mg/mL) | Total | 47.8 | 48.0 | 48.0 |
| IEC-content | Durvalumab | 47.9 | 47.7 | 47.6 |
| (mg/mL) | Tremelimumab | 2.3 | 2.3 | 2.3 |

Iron Ions Spiking Studies

The impact of iron ions to the stability of tremelimumab in the presence or absence of disodium edetate (EDTA) was also examined. Iron ions spiking stock was made by dissolving Iron (II) chloride (Alfa Aesar, Ward Hill, Mass.) in HPLC water to get 1000 ppm iron ions stock solution, which was further spiked into samples to get final desirable iron ions concentration. Samples of tremelimumab alone at 2 mg/mL with or without 0.03 mM EDTA in the 20:1 formulation composition (25 mM His/His-HCl, 270 mM trehalose dihydrate, 0.02% [w/v] polysorbate 80, pH 6.0) were spiked with iron ions (0, 100, 200, 500, or 1000 ppb) and incubated at 5, 25, or 40° C. Samples were analyzed by HPSEC, cIEF, CGE as appropriate.

FIGS. 21-26 show the monomeric purity loss of tremelimumab in the presence or absence of 0.03 mM EDTA with different levels of iron ions at 5, 25, or 40° C. At 40° C., monomeric purity percentage decreased over time with higher levels of iron ions. In the presence of EDTA, at both 5 and 25° C., no significant purity decreases were observed with up to 1ppm iron ions up to 9 months. However, when EDTA is absent, purity decreases were detected for samples with iron ions at all tested levels after incubated at either 5 or 25° C. for 3 months.

Figure 27:
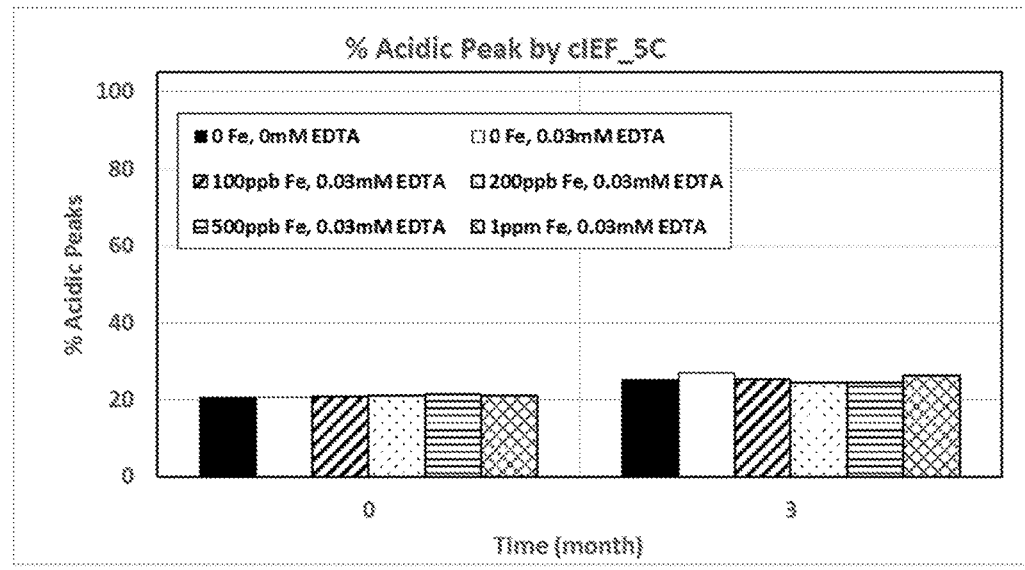
FIG. 27 is a graph depicting the acidic peak percentage of tremelimumab (in 20:1 formulation) as assessed by capillary isoelectric focusing (cIEF) when spiked with various levels of iron ions in the presence of EDTA at 5° C.
Figure 28:
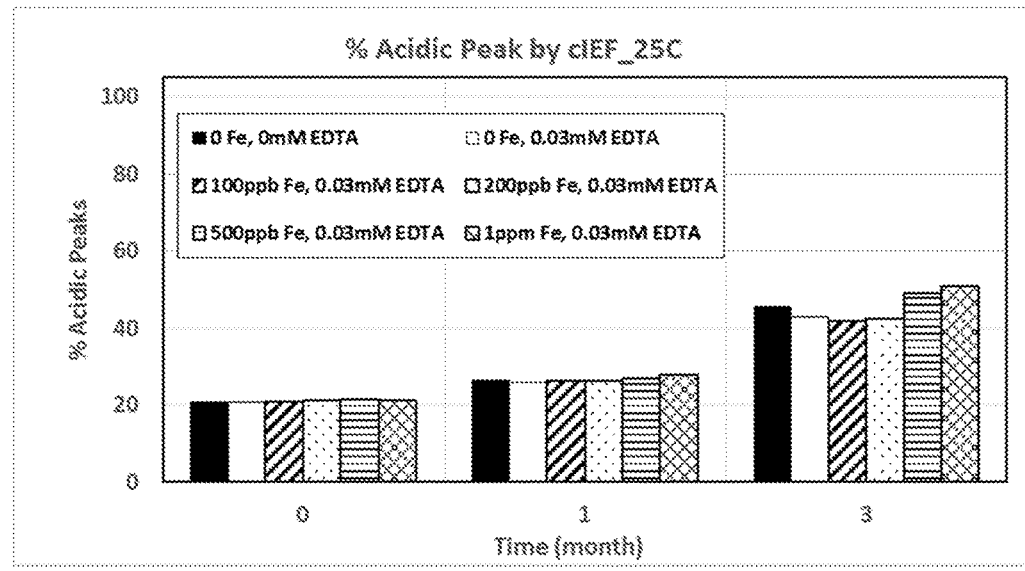
FIG. 28 is a graph depicting the acidic peak percentage of tremelimumab (in 20:1 formulation) as assessed by capillary isoelectric focusing (cIEF) when spiked with various levels of iron ions in the presence of EDTA at 25° C.
Figure 29:
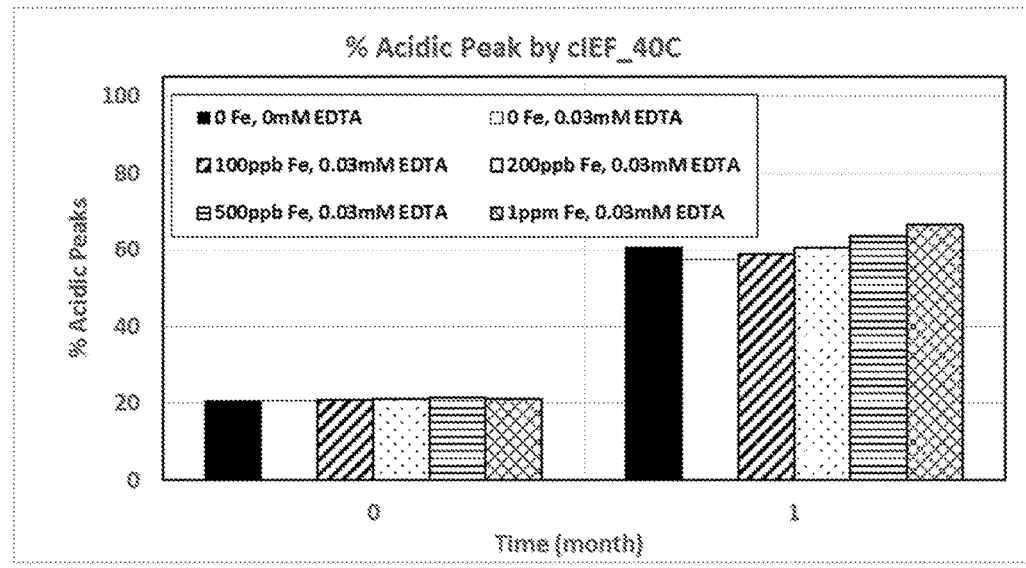
FIG. 29 is a graph depicting the acidic peak percentage of tremelimumab (in 20:1 formulation) as assessed by capillary isoelectric focusing (cIEF) when spiked with various levels of iron ions in the presence of EDTA at 40° C.

FIGS. 27-29 demonstrate the acidic peak profiles by cIEF for tremelimumab in the presence of EDTA with different levels of iron ions. As expected, acidic peak increased when incubated at elevated temperatures. However, no significant differences were observed for samples with different levels of iron ions. When EDTA is present, no significant acidic peak increase observed for samples with up to 1 ppm iron ions compared to sample without iron ions at 5° C. up to 3 months.

Figure 30:
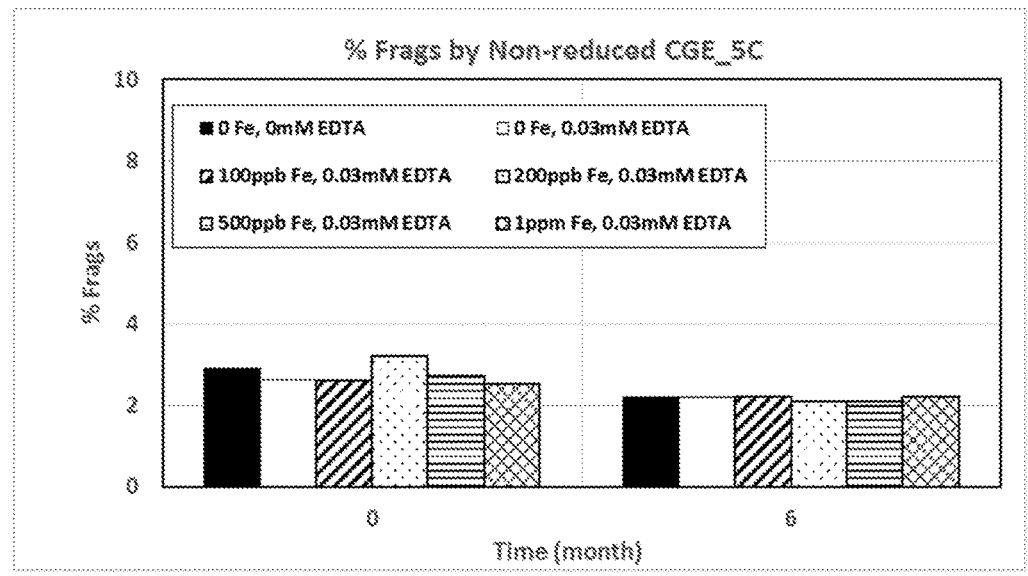
FIG. 30 is a graph depicting the fragment percentage of tremelimumab (in 20:1 formulation) as assessed by non-reduced capillary gel electrophoresis (CGE) when spiked with various levels of iron ions in the presence of EDTA at 5° C.
Figure 31:
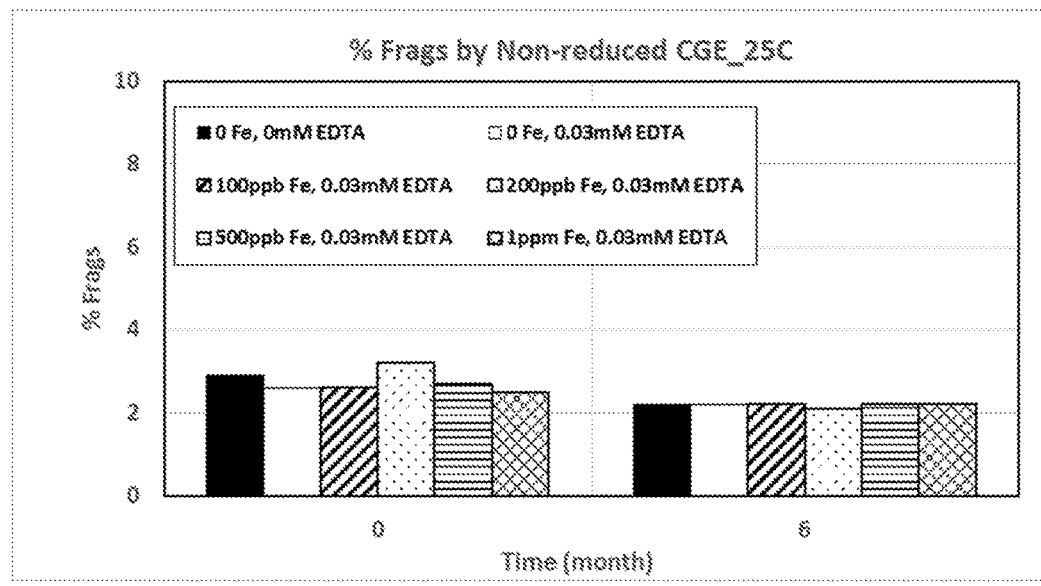
FIG. 31 is a graph depicting the fragment percentage of tremelimumab (in 20:1 formulation) as assessed by non-reduced capillary gel electrophoresis (CGE) when spiked with various levels of iron ions in the presence of EDTA at 25° C.

FIGS. 30-31 show the fragmentation profile of tremelimumab with different levels of iron ions when EDTA is present. At both 5 and 25° C., no significant increases in fragmentation were detected for samples with different levels of iron ions up to 6 months.

As shown in the studies described above, various methods indicate that the coformulated Durvalumab/Tremelimumab at a 20:1 ratio remains stable for an extended period of time. This helps to establish viability of the coformulation for use by clinicians in cancer treatment.

Example 2

Durvalumab and Tremelimumab Coformulation Potency

Potency of durvalimumab and tremelimumab in the coformulated product was determined using reporter gene bioassay methods specific for each component.

For determination of durvalumab potency, two-cell bioassay utilized anti-CD3 scFV (OKT3) and PD-L1 were expressed in a Chinese Hamster Ovary (CHO) cell line, and PD-1 and the reporter gene element (AP-1 luciferase) were expressed in a Jurkat human T-lymphocyte cell line (Jurkat PD-1 AP-1). The AP-1 signaling cascade was mediated in the Jurkat/PD-1 cells by co-stimulatory activation by anti-CD3 (via an anti-CD3 scFV[OKT3] expressed on the CHO cells) and anti-CD28 (added to the Jurkat/PD-1 assay media), resulting in the binding of the AP-1 transcription factor to the AP-1 DNA response element and the expression of the luciferase protein. Luminescence was quantified using a luminescence reader after reaction with the luciferase substrate. The amount of luminescence is proportional to the level of T-cell activation. The percent relative potency of the test sample was determined by dividing the IC50 value of the reference standard by the IC50 value of the test sample and multiplying by 100.

In the presence of PD-L1 expressed on the CHO cell line, the CD3/CD28 stimulatory signal was inhibited (T-cell suppression) and no luminescence signal was observed. In the presence of durvalumab, PD-L1 was inhibited from binding to PD-1, resulting in an increased luciferase signal due to restored CD3/CD28 stimulatory signal (restoration of T-cell activation). Potency of the coformulated sample to the durvalumab reference standard was quantified.

For determination of tremelimumab potency, the ability (potency) of coformulated product (containing tremelimumab) to attenuate CTLA-4-mediated inhibitory signal during T cell activation was measured. The assay consisted of two cell lines: a Jurkat cell line engineered to express IL-2-Luciferase and CTLA-4, and a Burkitt lymphoma derived lymphoblastoid cell line (Raji). In the presence of tremelimumab, CTLA-4-mediated inhibition of T-cell activation is attenuated, allowing for expression of the Luciferase reporter gene. The amount of luminescence is proportional to the T cell activity. Luminescence was quantified in a luminometer after reaction with the Steady-Glo luciferase substrate. The potency of the test sample is determined by dividing the $EC_{50}$ value of the tremelimumab reference standard by $EC_{50}$ value of the test sample.

For determination of tremelimumab potency, a two-cell assay was used; one cell was a Jurkat human T-cell lymphocyte cell line which had been engineered to express human CTLA4 and a luciferase reporter gene under the control of IL-2 promoter; the other was a human B lymphocyte Raji cell line that expressed B7. In principle, tremelimumab binds to the CTLA4 on the cell membrane resulting in blocking the inhibitory signal generated from CTLA4 pathway. In the presence of stimulator (anti- CD3 antibody, OKT3) and Raji cells, tremelimumab association with CTLA4 dose-dependently blocks B7 ligand binding to CTLA4 results in transcriptional activation of the IL2-luciferase reporter gene in the Jurkat cells. The amount of luminescence that is proportional to the T cell activity is quantified in a luminometer after reaction with the luciferase substrate. The percent relative potency of the test sample is determined by dividing the IC50 value of the reference standard by the IC50 value of the test sample and multiplying by 100.

Figure 12:
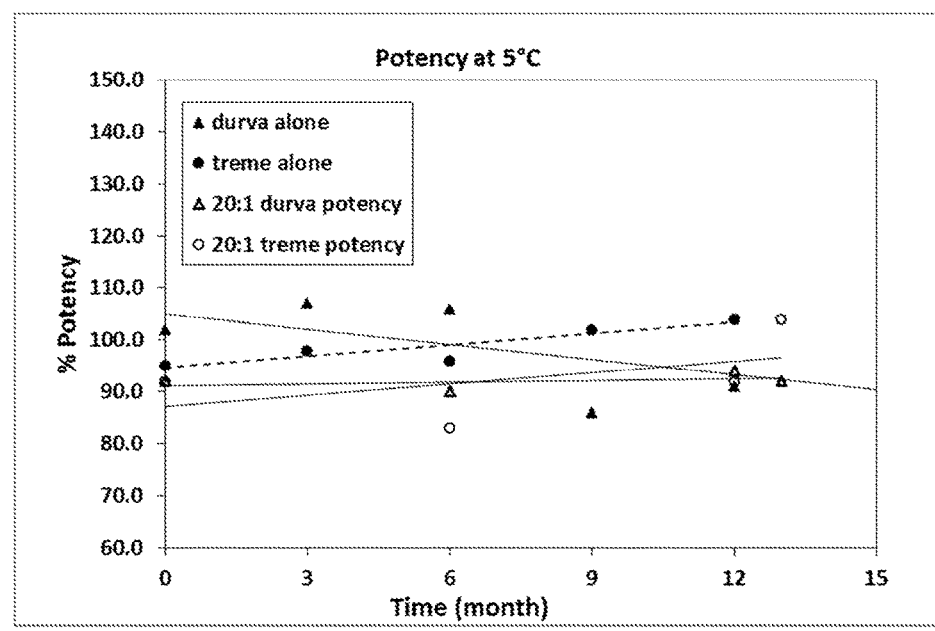
FIG. 12 is a graph depicting potency of either durvalumab or tremelimumab in coformulated 20:1 ratio when compared to durvalumab alone or tremelimumab alone at 5° C.
Figure 13:
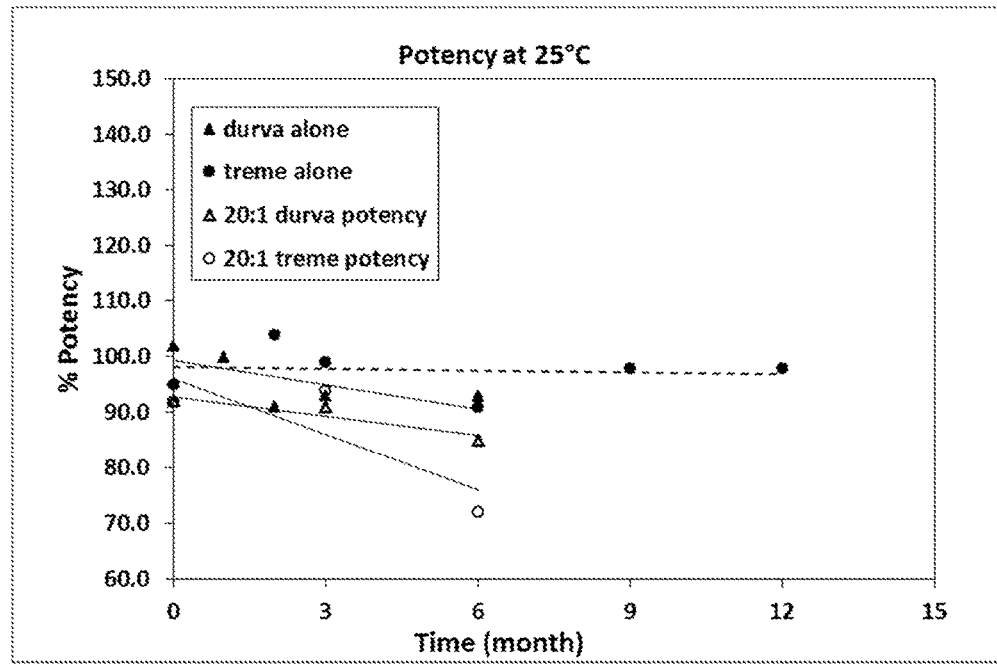
FIG. 13 is a graph depicting potency of either durvalumab or tremelimumab in coformulated 20:1 ratio when compared to durvalumab alone or tremelimumab alone at 25° C.
Figure 14:
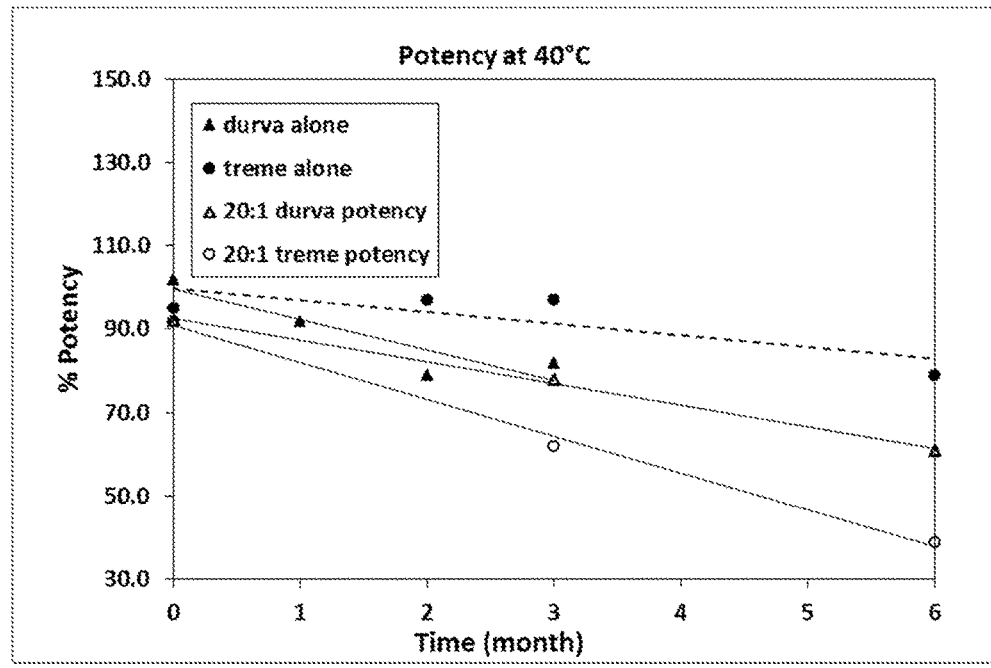
FIG. 14 is a graph depicting potency of either durvalumab or tremelimumab in coformulated 20:1 ratio when compared to durvalumab alone or tremelimumab alone at 40° C.
Figure 15:
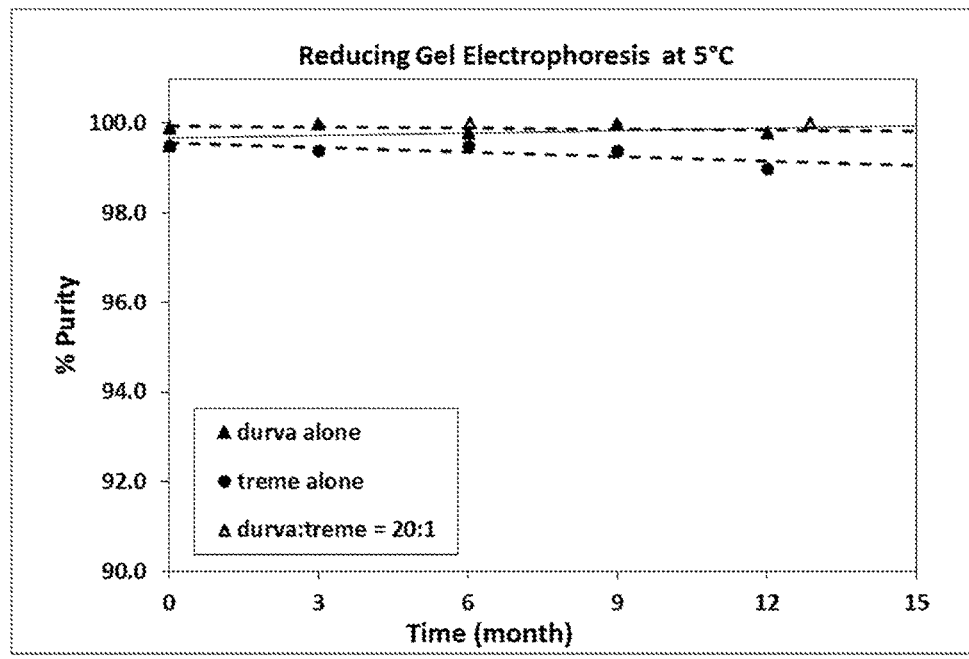
FIG. 15 is a graph depicting the main peak purity of coformulated durvalumab/tremelimumab at 20:1 ratio as assessed by reducing gel electrophoresis when compared to durvalumab alone or tremelimumab alone at 5° C.
Figure 16:
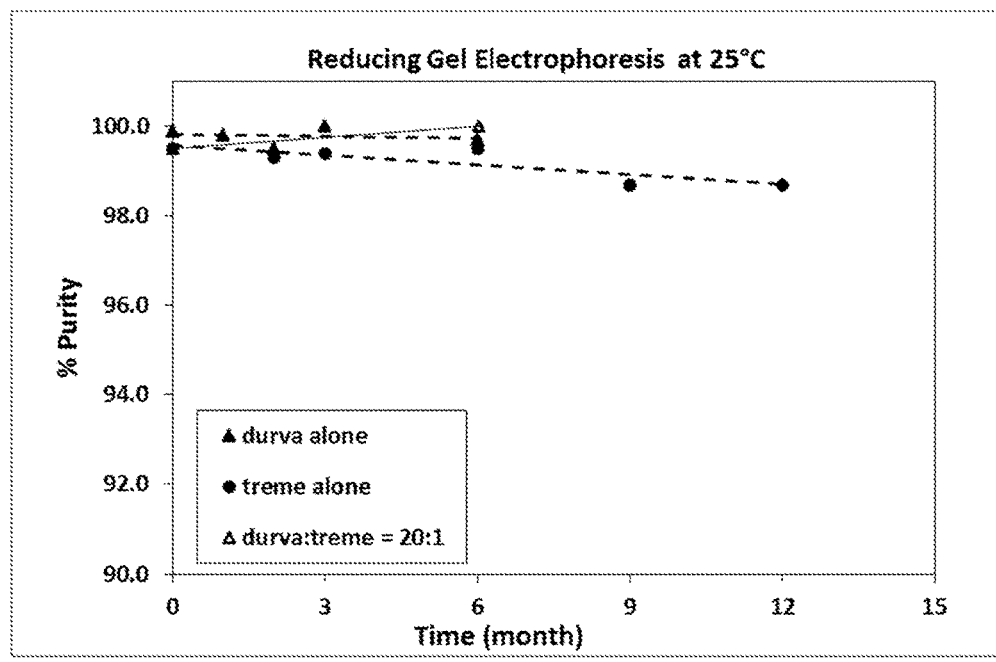
FIG. 16 is a graph depicting the main peak purity of coformulated durvalumab/tremelimumab at 20:1 ratio as assessed by reducing gel electrophoresis when compared to durvalumab alone or tremelimumab alone at 25° C.
Figure 17:
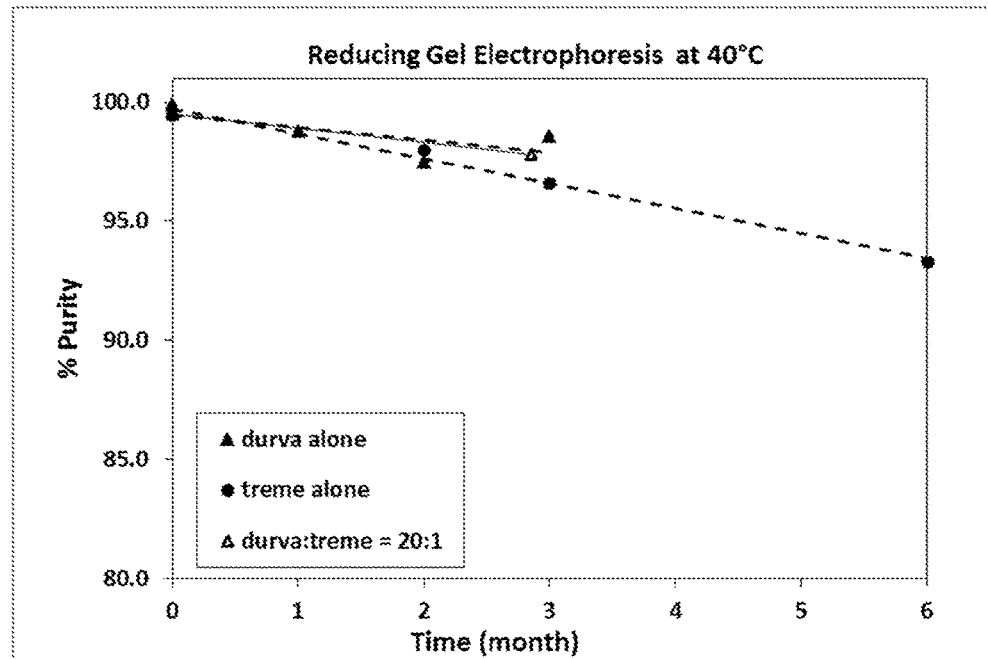
FIG. 17 is a graph depicting the main peak purity of coformulated durvalumab/tremelimumab at 20:1 ratio as assessed by reducing gel electrophoresis when compared to durvalumab alone or tremelimumab alone at 40° C.
Figure 18:
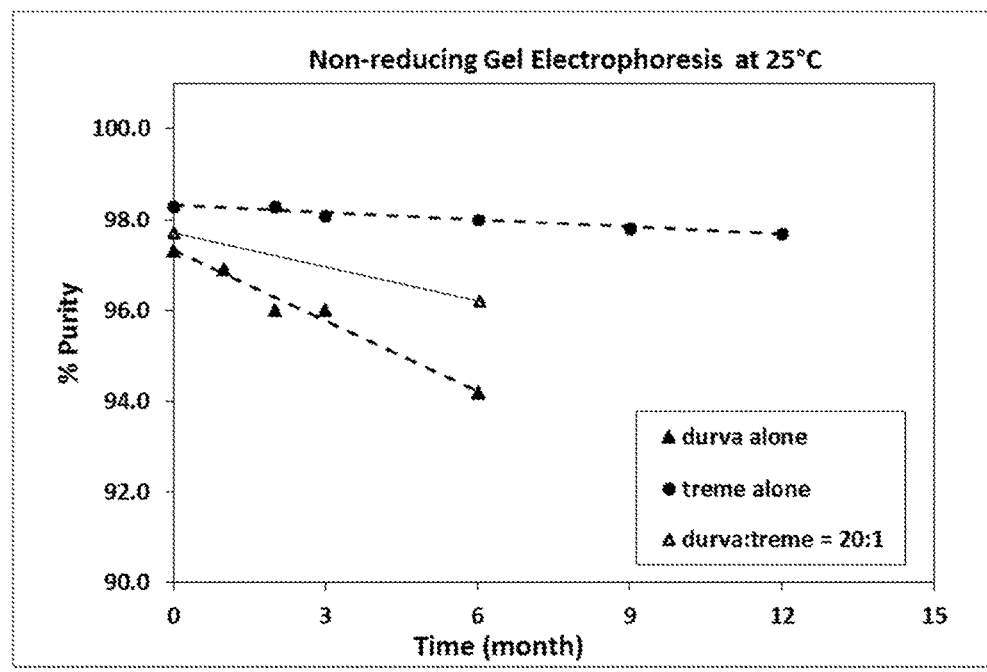
FIG. 18 is a graph depicting the main peak purity of coformulated durvalumab/tremelimumab at 20:1 ratio as assessed by non-reducing gel electrophoresis when compared to durvalumab alone or tremelimumab alone at 5° C.
Figure 19:
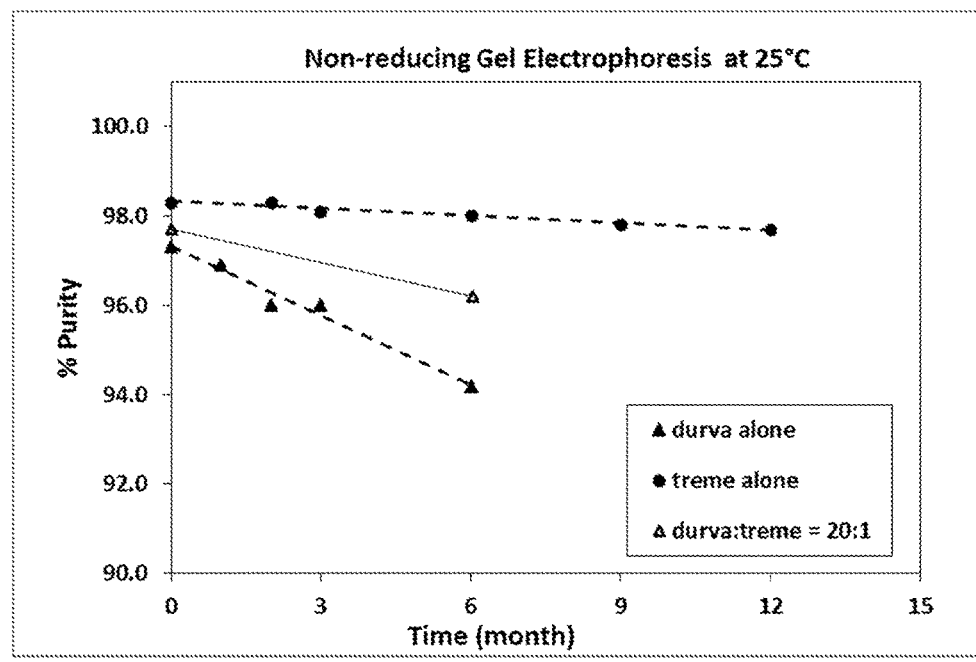
FIG. 19 is a graph depicting the main peak purity of coformulated durvalumab/tremelimumab at 20:1 ratio as assessed by non-reducing gel electrophoresis when compared to durvalumab alone or tremelimumab alone at 25° C.
Figure 20:
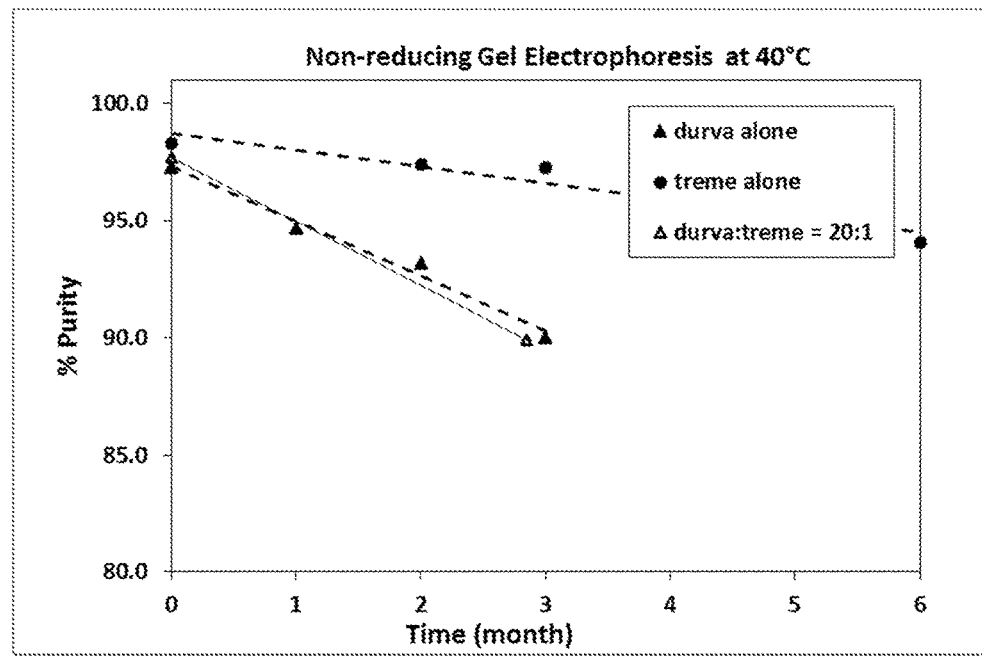
FIG. 20 is a graph depicting the main peak purity of coformulated durvalumab/tremelimumab at 20:1 ratio as assessed by non-reducing gel electrophoresis when compared to durvalumab alone or tremelimumab alone at 40° C.
Figure 21:
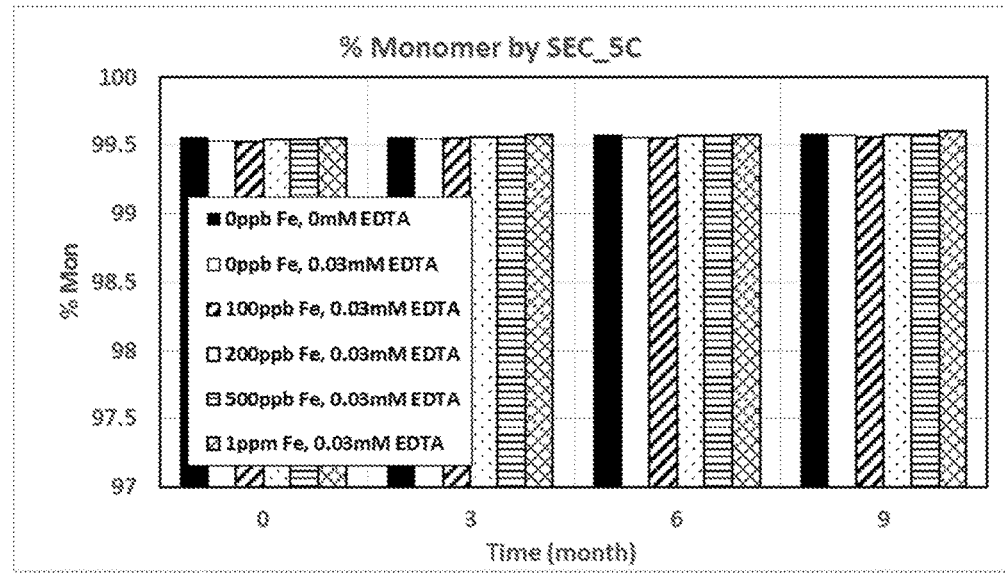
FIG. 21 is a graph depicting the purity of tremelimumab (in 20:1 formulation) as assessed by high performance size exclusion chromatography (HPSEC) when spiked with various levels of iron ions in the presence of EDTA at 5° C.
Figure 22:
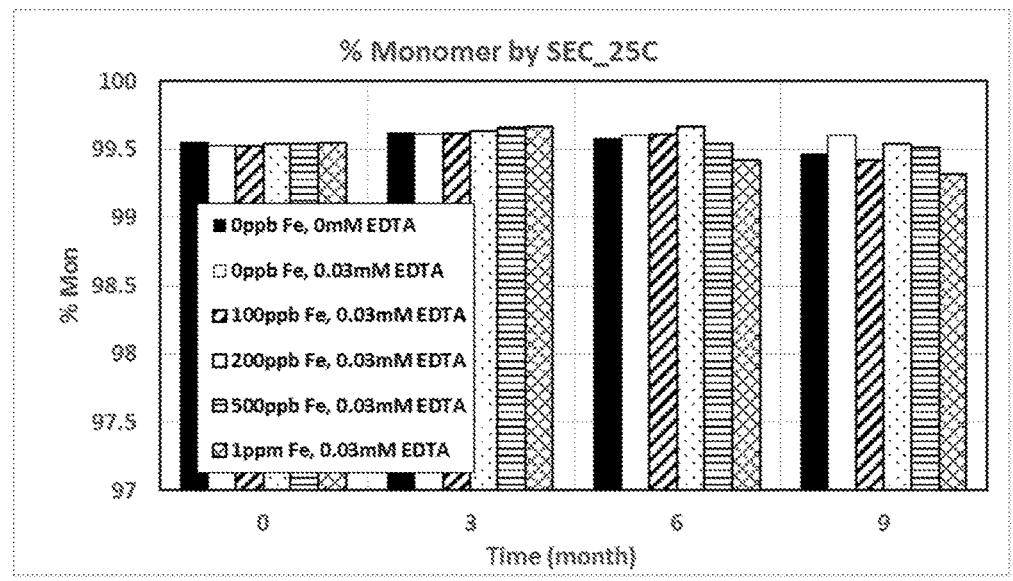
FIG. 22 is a graph depicting the purity of tremelimumab (in 20:1 formulation) as assessed by high performance size exclusion chromatography (HPSEC) when spiked with various levels of iron ions in the presence of EDTA at 25° C.
Figure 23:
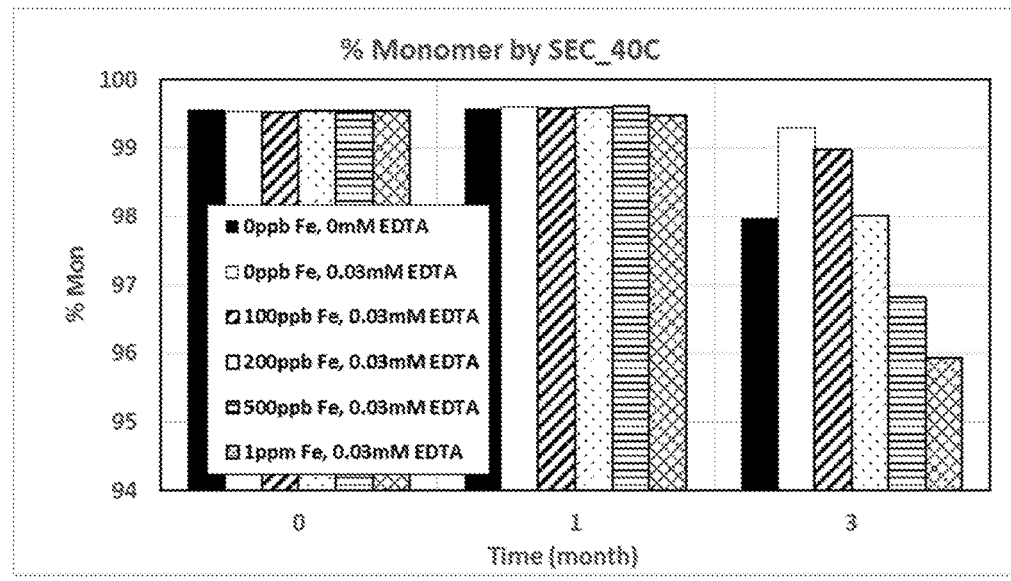
FIG. 23 is a graph depicting the purity of tremelimumab (in 20:1 formulation) as assessed by high performance size exclusion chromatography (HPSEC) when spiked with various levels of iron ions in the presence of EDTA at 40° C.
Figure 24:
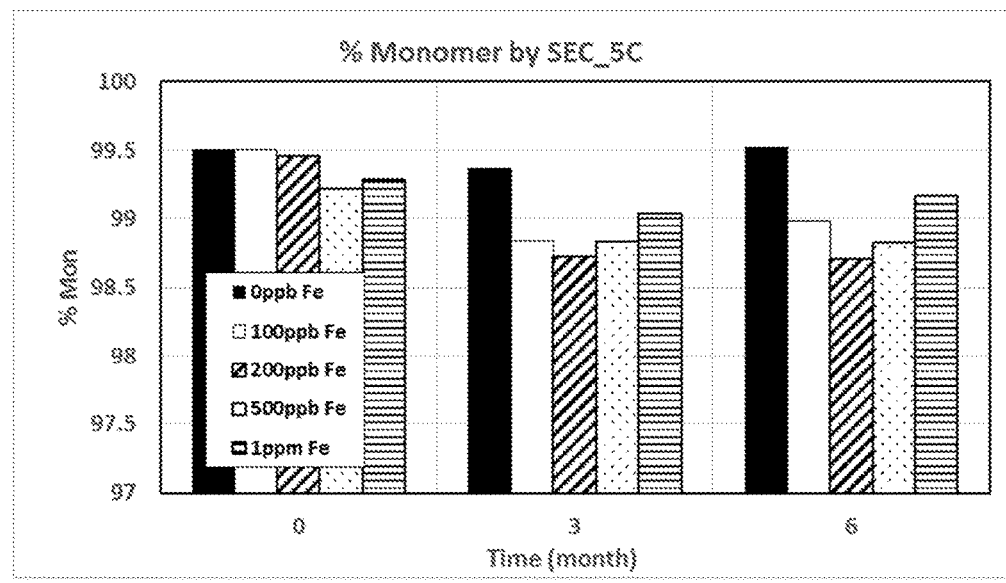
FIG. 24 is a graph depicting the purity of tremelimumab (in 20:1 formulation) as assessed by high performance size exclusion chromatography (HPSEC) when spiked with various levels of iron ions in the absence of EDTA at 5° C.
Figure 25:
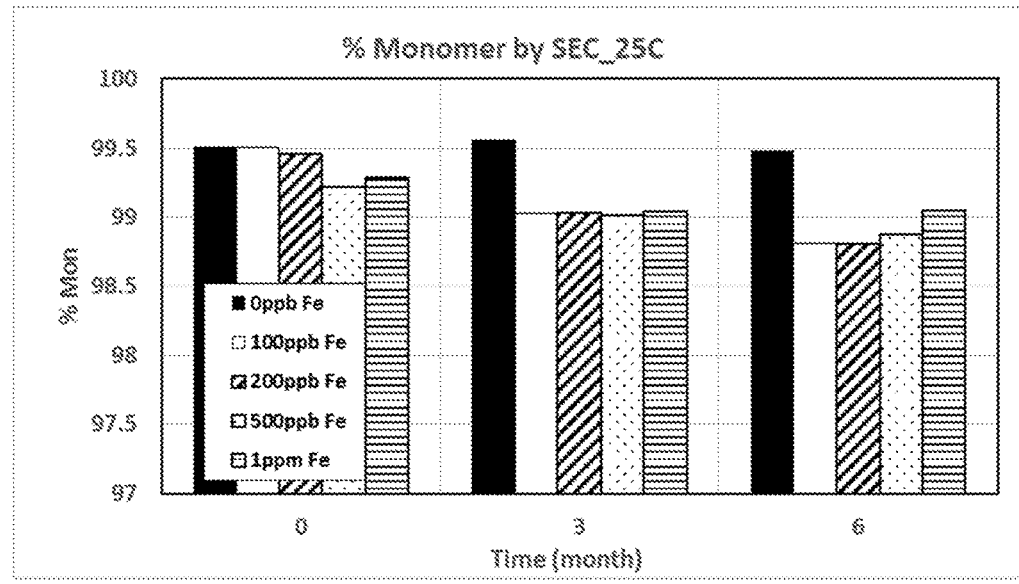
FIG. 25 is a graph depicting the purity of tremelimumab (in 20:1 formulation) as assessed by high performance size exclusion chromatography (HPSEC) when spiked with various levels of iron ions in the absence of EDTA at 25° C.
Figure 26:
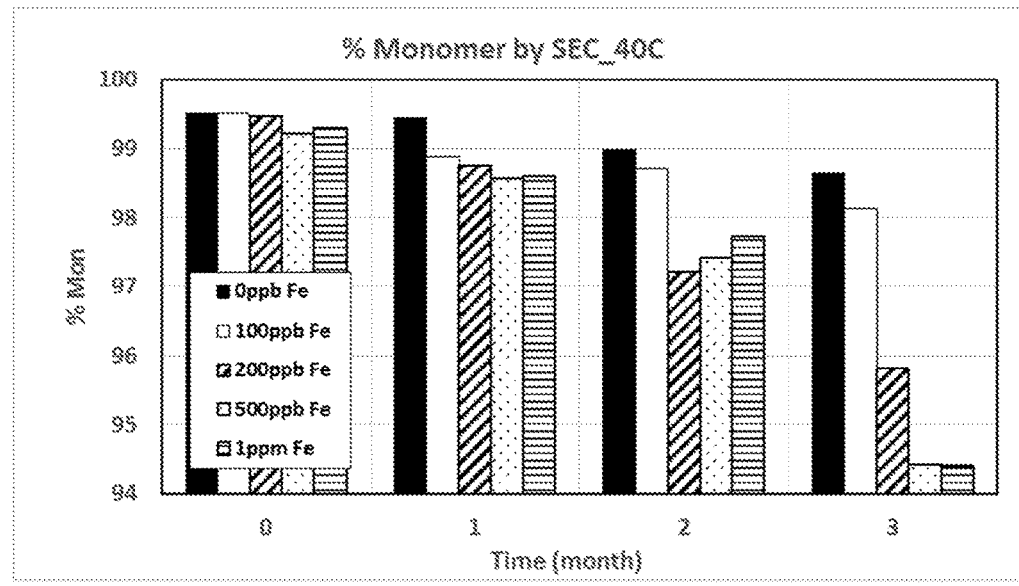
FIG. 26 is a graph depicting the purity of tremelimumab (in 20:1 formulation) as assessed by high performance size exclusion chromatography (HPSEC) when spiked with various levels of iron ions in the absence of EDTA at 40° C.

The potency of Durvalumab and Tremelimumab coformulated at 20:1 ratio was compared to Durvalumab and Tremelimumab alone at various temperatures (5° C., 25° C., and 40° C.). Potency was determined using the reporter gene assay described in more detail above. As shown in FIGS. 12-14, the Durvalumab/Tremelimumab 20:1 coformulation exhibited similar potency as the corresponding antibodies alone over twelve months when stored at 5° C. (FIG. 12), over six months when stored at 25° C. (FIG. 13), and over three months when stored at 40° C. (FIG. 14).

The studies described above show that the Durvalumab/Tremelimumab 20:1 coformulation is as potent as combination administration, thus providing a significant benefit for cancer patients.

Those skilled in the art will recognize, or be able to ascertain using no more than routine experimentation, many equivalents to the specific aspects of the disclosure described herein. Such equivalents are intended to be encompassed by the following claims.

Although the foregoing invention has been described in some detail by way of illustration and example for purposes of clarity of understanding, it will be obvious that certain changes and modifications can be practiced within the scope of the appended claims.

Various publications are cited herein, the disclosures of which are incorporated by reference in their entireties.

The following references are cited herein:

REFERENCES

1. Gajewski T F, Schreiber H, Fu Y X. Innate and adaptive immune cells in the tumor microenvironment. *Nat Immunol* 2013; 14: 1014-22.
2. Kvistborg P, Philips D, Kelderman S, et al. Anti-CTLA-4 therapy broadens the melanoma-reactive CD8+ T cell response. *Sci Transl Med* 2014; 6:254ra128.
3. Larkin J, Chiarion-Sileni V, Gonzalez R, et al. Combined nivolumab and ipilimumab or monotherapy in untreated melanoma. *N Engl J Med* 2015; 373: 23-34.
4. Antonia S J, Gettinger S N, Chow LQM, et al. Nivolumab (anti-PD-1; BMS-936558, ONO-4538) and ipilimumab in first-line NSCLC: Interim phase I results. *J Clin Oncol* 2014; 32: Suppl:8023. abstract.
5. MedImmune/AstraZeneca, Data on file. 2015.
6. Matsumoto K, Fukuyama S, Eguchi-Tsuda M, et al. B7-DC induced by IL-13 works as a feedback regulator in the effector phase of allergic asthma. *Biochem Biophys Res Commun* 2008; 365: 170-5.
7. Matsumoto K, Inoue H, Nakano T, et al. B7-DC regulates asthmatic response by an IFN-gamma-dependent mechanism. *J Immunol* 2004; 172: 2530-41.
8. Rizvi N, Brahmer J, Ou S-HI. Safety and clinical activity of MEDI4736, an anti-programmed cell death-ligand 1 (PD-L1) antibody, in patients with non-small cell lung cancer (NSCLC). *J Clin Oncol* 2015; 33: Suppl:8032. abstract.
9. Ribas A, Camacho L H, Lopez-Berestein G, et al. Antitumor activity in melanoma and anti-self responses in a phase I trial with the anti-cytotoxic T lymphocyte-associated antigen 4 monoclonal antibody CP-675,206. *J Clin Oncol* 2005; 23: 8968-77.
10. Tarhini A A. Tremelimumab: a review of development to date in solid tumors. Immunotherapy 2013; 5: 215-29.
11. Stewart R, Mullins S, Watkins A, et al. Preclinical modeling of immune checkpoint blockade (P2012). *J Immunol* 2013; 190: Suppl:214.7.
12. Huang X, Biswas S, Oki Y, Issa JP, Berry DA. A parallel phase I/II clinical trial design for combination therapies. *Biometrics* 2007; 63: 429-36.
13. Eisenhauer E A, Therasse P, Bogaerts J, et al. New response evaluation criteria in solid tumours: revised RECIST guideline (version 1.1). *Eur J Cancer* 2009; 45: 228-47.
14. Rebelatto M, Mistry A, Sabalos C, et al. Development of a PD-L1 companion diagnostic assay for treatment with MEDI4736 in NSCLC and SCCHN patients. *J Clin Oncol* 2015; 33:Suppl: 8033. abstract.
15. Song X, Pak M, Chavez C, et al. Population pharmacokinetics of MEDI4736, a fully human anti-programmed death ligand 1 (PD-L1) monoclonal antibody, in patients with advanced solid tumors. European Cancer Congress 2015 Sep. 25-29; Vienna, Austria: ECC; 2015. Abstract 203.
16. Pan ZK, Ye F, Wu X, An HX, Wu JX. Clinicopathological and prognostic significance of programmed cell death ligand1 (PD-L1) expression in patients with non-small cell lung cancer: a meta-analysis. *J Thorac Dis* 2015; 7: 462-70.
17. Zatloukal P, Heo D S, Park K, et al. Randomized phase II clinical trial comparing tremelimumab (CP-675,206) with best supportive care (BSC) following first-line platinum-based therapy in patients (pts) with advanced non-small cell lung cancer (NSCLC). *J Clin Oncol* 2009; 27:Suppl: 8071. abstract.
18. Lutzky J, Antonia S J, Blake-Haskins A, et al. A phase 1 study of MEDI4736, an anti-PD-L1 antibody, in patients with advanced solid tumors. J Clin Oncol 2014; 32:Suppl: 3001. abstract.
19. Antonia S J, Gettinger S N, Chow L, et al. Nivolumab (anti-PD-1; BMS-936558, ONO-4538) and ipilimumab in first-line NSCLC: Interim phase I results. *J Clin Oncol* 2014;32: Suppl: 8023. abstract.
20. Antonia S J, Larkin J, Ascierto PA. Immuno-oncology combinations: a review of clinical experience and future prospects. *Clin Cancer Res* 2014; 20: 6258-68.
21. Swanson M S, Sinha UK. Rationale for combined blockade of PD-1 and CTLA-4 in advanced head and neck squamous cell cancer-review of current data. *Oral Oncol* 2015; 51: 12-5.
22. Wolchok J D, Kluger H, Callahan M K, et al. Nivolumab plus ipilimumab in advanced melanoma. *N Engl J Med* 2013; 369: 122-33.

What is claimed is:

1. A composition comprising durvalumab, or an antigen-binding fragment thereof, and tremelimumab, or an antigen-binding fragment thereof, wherein the concentration of durvalumab, or an antigen-binding fragment thereof, is about 18.7 mg/mL to about 44.4 mg/mL and wherein the concentration of tremelimumab, or an antigen-binding fragment thereof, is about 2.2 mg/mL to about 12.5 mg/mL.

2. The composition of claim 1, wherein the concentration of durvalumab, or an antigen-binding fragment thereof, is about 18.7 mg/mL, 36.3 mg/mL, 40.0 mg/mL, 42.8 mg/mL, or 44.4 mg/mL.

3. The composition of claim 1, wherein the concentration of tremelimumab, or an antigen-binding fragment thereof, is about 2.2 mg/mL, 2.9 mg/mL, 4.0 mg/mL, 5.5 mg/mL, or 12.5 mg/mL.

4. The composition of claim 1, wherein the combined concentration of durvalumab, or an antigen-binding fragment thereof, and tremelimumab, or an antigen-binding fragment thereof, is about 31.2 mg/mL to about 46.6 mg/mL.

5. The composition of claim 1, wherein the combined concentration of durvalumab, or an antigen-binding fragment thereof, and tremelimumab, or an antigen-binding fragment thereof, is about 31.2 mg/mL, 41.8 mg/mL, 44.0 mg/mL, 45.7 mg/mL, or 46.6 mg/mL.

6. The composition of claim 1, wherein the concentration ratio of durvalumab to tremelimumab is from about 15:10 to about 20:1.

7. The composition of claim 6, wherein the concentration ratio of durvalumab to tremelimumab is about 20:1.

8. The composition of claim 1, further comprising Histidine, Histidine-HCl, or a combination thereof.

9. The composition of claim 8, wherein the concentration of the Histidine, Histidine-HCl, or a combination thereof, is from about 20 mM to about 25 mM.

10. The composition of claim 1, further comprising trehalose dihydrate.

11. The composition of claim 10, wherein the concentration of the trehalose dihydrate is from about 254 mM to about 269 mM.

12. The composition of claim 1, further comprising Ethylenediaminetetraacetic acid (EDTA).

13. The composition of claim 12, wherein the concentration of EDTA is from about 0.03 mM to about 0.17 mM.

14. The composition of claim 1, further comprising polysorbate 80 (PS80).

15. The composition of claim 14, wherein the concentration of polysorbate 80 is about 0.02 percent weight/volume (% w/v).

16. The composition of claim 1, having a pH of about 6.0.

17. A pharmaceutical composition comprising or consisting of about 44.4 mg/mL durvalumab, or an antibody fragment thereof, about 2.2 mg/mL tremelimumab, or an antibody fragment thereof, about 25 mM Histidine/Histidine-HCl, about 269 mM Trehalose dehydrate, about 0.03 mM EDTA, and about 0.02% w/v PS80 at a pH of about 6.0.

18. The composition of claim 1, formulated for intravenous injection.

19. A kit comprising the composition of claim 1, and instructions for use in the treatment of a solid tumor, cancer, lung cancer, or non-small cell lung cancer (NSCLC).

* * * * *